US012576035B2

(12) United States Patent
Kovarova et al.

(10) Patent No.: US 12,576,035 B2
(45) Date of Patent: Mar. 17, 2026

(54) POLYMERIC IMPLANTS WITH HIGH DRUG LOADING AND LONG-ACTING DRUG RELEASE AND METHODS OF MAKING THE SAME

(71) Applicant: The University of North Carolina at Chapel Hill, Chapel Hill, NC (US)

(72) Inventors: Martina Kovarova, Chapel Hill, NC (US); Soumya Rahima Benhabbour, Chapel Hill, NC (US); J. Victor Garcia-Martinez, Durham, NC (US); Panita Maturavongsadit, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 184 days.

(21) Appl. No.: 17/427,190

(22) PCT Filed: Jan. 31, 2020

(86) PCT No.: PCT/US2020/016061
§ 371 (c)(1),
(2) Date: Jul. 30, 2021

(87) PCT Pub. No.: WO2020/160379
PCT Pub. Date: Aug. 6, 2020

(65) Prior Publication Data
US 2022/0105042 A1     Apr. 7, 2022

Related U.S. Application Data

(60) Provisional application No. 62/800,087, filed on Feb. 1, 2019.

(51) Int. Cl.
*A61K 9/20*     (2006.01)
*A61K 9/00*     (2006.01)
*A61K 45/06*     (2006.01)

(52) U.S. Cl.
CPC ............ *A61K 9/204* (2013.01); *A61K 9/0024* (2013.01); *A61K 9/2095* (2013.01); *A61K 45/06* (2013.01)

(58) Field of Classification Search
None
See application file for complete search history.

(56) References Cited

U.S. PATENT DOCUMENTS 4,761,289 A  *  8/1988  Shalati ................ A61K 9/0024
424/475
5,702,716 A     12/1997  Dunn et al.

8,524,829 B2     9/2013  Mathiowitz et al.
2004/0070093 A1     4/2004  Mathiowitz et al.
2014/0328835 A1*  11/2014  Whitcup .............. A61K 9/0024
424/133.1
2016/0279069 A1     9/2016  Jayant et al.
2017/0080092 A1     3/2017  Cleland et al.

FOREIGN PATENT DOCUMENTS

EP           1917957 A2 *  5/2008  ............... A61F 2/00
WO          2008099278 A2     8/2008
WO     WO 2012/085284 A3     6/2012
WO     WO 2020/160379 A1     8/2020

OTHER PUBLICATIONS

Notification Concerning Availability of the Publication of the International Application Corresponding to International Application No. PCT/US 2020/016061 dated Aug. 6, 2020.
International Search Report Corresponding to International Application No. PCT/US 2020/016061 dated May 7, 2020 and Written Opinion of the International searching Authority Corresponding to International Application No. PCT/US 2020/016061 dated May 7, 2020.
International Preliminary Report on Patentability Corresponding to International Application No. PCT/US 2020/016061 dated Jul. 27, 2021.
Baert et al., "Development of a long-acting injectable formulation with nanoparticles of rilpivirine (TMC278) for HIV treatment." Eur. J. Pharm. Biopharm., vol. 72, pp. 502-508 (2009).
Barnhart, "Long-Acting HIV Treatment and Prevention: Closer to the Threshold." Global Health: Science and Practice, vol. 5, pp. 182-187 (2017).
Garcia-Lerma et al., "Animal models of antiretroviral prophylaxis for HIV prevention." Current Opinion in HIV and AIDS, vol. 7, pp. 505-513 (2012).
Grant et al., "Preexposure chemoprophylaxis for HIV prevention in men who have sex with men." N. Engl. J. Med., vol. 363, pp. 2587-2599 (2010).
Gunawardana et al., "Pharmacokinetics of Long-Acting Tenofovir Alafenamide (GS-7340) Subdermal Implant for HIV Prophylaxis." Antimicrob. Agents Chemother., vol. 59, pp. 3913-3919 (2015).

(Continued)

*Primary Examiner* — Anna R Falkowitz
*Assistant Examiner* — Edwin Coleman Mitchell
(74) *Attorney, Agent, or Firm* — KDW FIRM PLLC

(57)     ABSTRACT

Disclosed herein are polymeric implants and controlled release drug delivery systems to provide high drug loading and long-acting drug release. Provided herein are methods for making the same. Methods of administering pharmacologically active agents via the disclosed polymeric implants and controlled release drug delivery systems are also provided.

14 Claims, 21 Drawing Sheets

(56)           References Cited

OTHER PUBLICATIONS

Landovitz et al., "The Promise and Pitfalls of Long Acting Injectable Agents for HIV Prevention." Current Opinion in HIV and AIDS, vol. 11, pp. 122-128 (2016).

Marrazzo et al., "Tenofovir-based preexposure prophylaxis for HIV infection among African women." N. Engl. J. Med., vol. 372, pp. 509-518 (2015).

Parent et al., "PLGA In situ implants formed by phase inversion: Critical physiochemical parameters to modulate drug release." Journal of Controlled Release, vol. 172(1), pp. 292-304 (2013).

Rabin et al., "In vitro and in vivo demonstration of risperidone implants in mice." Schizophr. Res., vol. 98, pp. 66-78 (2008).

Schlesinger et al., "A Tunable, Biodegradable, Thin-Film Polymer Device as a Long-Acting Implant Delivering Tenofovir Alafenamide Fumarate for HIV Pre-exposure Prophylaxis." Pharm. Res., vol. 33, pp. 1649-1656 (2016).

Siegel et al., "Effect of drug type on the degradation rate of PLGA matrices." Eur. J. Pharm. Biopharm., vol. 64, pp. 287-293 (2006).

Wang et al., "A rapid method for creating drug implants: translating laboratory-based methods into a scalable manufacturing process." Journal of biomedical materials research. Part B, Applied biomaterials, vol. 93, pp. 562-572 (2010).

Widmer et al., "Manufacture of porous biodegradable polymer conduits by an extrusion process for guided tissue regeneration." Biomaterials, vol. 19, pp. 1945-1955 (1998).

National Institute of Allergy and Infectious Diseases, "Antiretroviral Drug Discovery and Development," (2024) Retrieved from <URL: https://www.nih.gov/diseases-conditions/antiretroviral-drug-development>.

Shangraw et al., "Compressed tablets by direct compression," Pharmaceutical Dosage Forms: Tablets, Chapter 4: 195-246 (Jan. 1989).

* cited by examiner

Overview cross-section

Outer layer

Core

D

POLYMERIC IMPLANTS WITH HIGH DRUG LOADING AND LONG-ACTING DRUG RELEASE AND METHODS OF MAKING THE SAME

CROSS-REFERENCE TO RELATED APPLICATIONS

This application claims benefit of U.S. Provisional Patent Application Ser. No. 62/800,087, filed Feb. 1, 2019, herein incorporated by reference in its entirety.

STATEMENT OF FEDERAL SUPPORT

This invention was made with government support under grant number 1R01AI131430-01 awarded by National Institutes of Health. The government has certain rights to this invention.

TECHNICAL FIELD

Embodiments of the present disclosure relate generally to the development and use of long-acting biodegradable polymeric implants.

BACKGROUND

HIV is the sixth leading cause of death in the world and the third leading cause of death as a communicable disease.[1] Despite decades of research, globally ~37 million people are living with HIV and ~2.0 million people are newly infected with the virus every year.[2] Antiretroviral Therapy (ART) is highly recommended for Individuals who have HIV. However, ARTs are currently dominated by a daily co-administration of oral antiretroviral drugs (i.e. Stribild®, Genvoya®, Triumeq®) leading to low patient adherence, increased risk of drug resistance, and treatment failure. In addition, a preventative method of HIV infection, Pre-Exposure Prophylaxis (PrEP), is highly recommended for high-risk individuals. However, the current method of HIV PrEP is limited to a daily oral pill treatment (Truvada®) leading to low patient adherence and variable efficacy.[3, 4] Cost constraints and uneven access to ART/PrEP across the world further limit the benefits of current HIV PrEP/ART formulations.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, provided herein are methods of making a polymeric implant comprising forming a homogeneous drug-loaded polymer, wherein forming the homogenous drug-loaded polymer comprises utilizing a phase inversion technique comprising introducing a solution comprising (a) a biodegradable polymer, (b) a water miscible biocompatible organic solvent, (c) at least one pharmaceutically active agent, and optionally (d) a release rate-limiting additive to an aqueous medium wherein the solvent diffuses into the aqueous medium during phase inversion providing an insoluble solid composition comprising the pharmaceutically active agent and the polymer, micronizing the insoluble solid composition, and utilizing direct compression of the micronized insoluble solid composition to form a solid tablet forming the polymeric implant.

In some aspects, the biodegradable polymer is selected from the group consisting of poly(lactic-co-glycolic acid) (PLGA), poly(lactic acid) (PLA), polycaprolactone (PCL), polylactic acid (PLA), polyglycolic acid (PGA), poly(butylene succinate) (PBS), and sucrose acetate isobutyrate (SAIB). In some aspects, the biodegradable polymer is poly(lactic-co-glycolic acid) (PLGA).

In some aspects, the water miscible biocompatible organic solvent is selected from the group consisting of N-methyl-2-pyrrolidone (NMP), dimethyl sulfoxide (DMSO), polyethylene glycol (PEG), acetone, methanol, Labrasol®, and Tween®. In some aspects, the water miscible biocompatible organic solvent consists of a combination of two solvents from the group consisting of NMP, DMSO, Gelucire®, polyethylene glycol (PEG), Labrasol®, Tween®, Brij® 78, Triacetin, Pluronics® and Vitamin E TPGS.

In some embodiments, the ratio of biodegradable polymer to water miscible biocompatible organic solvent is from 1:2, 1:3, 1:4, 1:5 1:6, 1:7 1:8, 1:9 or 1:10. The at least one pharmaceutically active agent can be selected from the group consisting of an analgesic agent; an anti-anxiety agent; an anti-arthritic agent; an anti-asthmatic agent; an anticancer agent; an anticholinergic agent; an anticholinesterase; an anticonvulsant; an antidepressant; an antidiabetic agent; an antidiarrheal agent; an anti-emetic agent; an antihistamine; an antihyperlipidemic agent; an anti-infective agent; an anti-inflammatory agent; an antimigraine agent; an anti-obesity agent; an antipruritic agent; an antipsychotic agent; an antiretroviral agent, an antispasmodic agent; an agent for treating a neurodegenerative disease; a cardiovascular medicament; contraceptive agent, a diuretic agent; a gastrointestinal medication; a hormone or anti-hormone; a hypnotic agent; an immunosuppressive agent; a leukotriene inhibitor; a narcotic agonist or antagonist; a neurotransmitter; a nucleic acid; a nutrient; a peptide drug; a nutrient; a sympathomimetic agent; a thrombolytic agent; a vasodilator; or a combination thereof. In some aspects, the at least one pharmaceutically active agent is at least one antiretroviral agent. In some aspects, the at least one pharmaceutically active agent is a combination of at least two drugs, at least one drug comprising an antiretroviral agent. In some aspects, at least one drug comprises a contraceptive agent.

In some embodiments, the tablet can be formed into various shapes and sizes. In some aspects, the tablet is in the shape of a rod, a square, a sphere, a disk, a star, a round shape, Y-shape, T-shape, U-shape or an undefined shape.

Provided herein are polymeric implants formed according to the methods disclosed herein. In some aspects, the polymeric implants can be a solvent-free polymeric implant.

Also provided herein are controlled release drug delivery systems comprising an implantable or administered device that provides controlled release of at least one pharmaceutically active agent throughout an extended drug delivery time period, the implantable device comprising a drug-loaded polymer formed by a process comprising utilizing a phase inversion technique comprising introducing a solution comprising (a) a biodegradable polymer, (b) a water miscible biocompatible organic solvent, (c) at least one pharmaceutically active agent, and optionally (d) a release rate-limiting agent to an aqueous medium wherein the solvent diffuses into the aqueous medium during phase inversion to provide an insoluble solid composition comprising the pharmaceutically active agent and the polymer, micronizing the insoluble solid composition, and utilizing direct compression of the micronized insoluble solid composition to form the implantable device, wherein following implantation or administration of the device into a subject, the device results in a serum level of the pharmaceutically active agent sufficient to achieve therapeutic efficacy during the extended drug delivery time period.

In some aspects, the ratio of biodegradable polymer to water miscible biocompatible organic solvent is from 1:2, 1:3, 1:4, 1:5, 1:6, 1:7, 1:8, 1:9 or 1:10. In some aspects, the insoluble solid composition comprising the pharmaceutically active agent and the polymer is formed in situ. In some aspects, the biodegradable polymer is selected from the group consisting of poly(lactic-co-glycolic acid) (PLGA), poly(lactic acid) (PLA), poly(glycolic acid) (PGA), poly-caprolactone (PCL), poly(butylene succinate) (PBS) or a combination thereof. In some aspects, the biodegradable polymer is poly(lactic-co-glycolic acid) (PLGA). In some aspects, the water miscible biocompatible organic solvent is selected from the group consisting of N-methyl-2-pyrrolidone (NMP), dimethyl sulfoxide (DMSO), polyethylene glycol (PEG), acetone, methanol, Labrasol®, Gelucire®, pluronics and Tween®.

In some embodiments, multiple pharmaceutical agents (e.g. 2-8) are combined in a single tablet. In some aspects, multiple pharmaceutical agents (e.g. 2-8) are combined in sandwiched (stacked) tablets. In some aspects, the at least one pharmaceutically active agent is selected from the group consisting of an analgesic agent; an anti-anxiety agent; an anti-arthritic agent; an anti-asthmatic agent; an anticancer agent; an anticholinergic agent; an anticholinesterase; an anticonvulsant; an antidepressant; an antidiabetic agent; an antidiarrheal agent; an anti-emetic agent; an antihistamine; an antihyperlipidemic agent; an anti-infective agent; an anti-inflammatory agent; an antimigraine agent; an anti-obesity agent; an antipruritic agent; an antipsychotic agent; an antiretroviral agent, an antispasmodic agent; an agent for treating a neurodegenerative disease; a cardiovascular medicament; a contraceptive agent, a diuretic agent; a gastrointestinal medication; a hormone or anti-hormone; a hypnotic agent; an immunosuppressive agent; a leukotriene inhibitor; a narcotic agonist or antagonist; a neurotransmitter; a nucleic acid; a nutrient; a peptide drug; a nutrient; a sympathomimetic agent; a thrombolytic agent; a vasodilator; or a combination thereof.

In some aspects, the at least one pharmaceutically active agent is at least one antiretroviral agent. In some aspects, the at least one pharmaceutically active agent is a combination of at least two drugs, at least one drug comprising an antiretroviral agent. In some aspects, at least one drug comprises a contraceptive agent.

In some embodiments, the tablet can be formed into various shapes and sizes. In some aspects, the tablet is in the shape of a rod, a square, a sphere, a disk, a star, a round shape, Y-shape, T-shape, U-shape or an undefined shape.

In some aspects, the pharmacologically active agent is released at a rate that is substantially constant throughout the effective drug delivery time period. In some aspects, the effective drug delivery time period is in the range of about six months to about to about 1 year. In some aspects, the subject is afflicted with, susceptible to, or considered high risk for a communicable disease. In some aspects, the communicable disease is a human immunodeficiency virus (HIV).

Provided herein are methods for administering a pharmacologically active agent to a subject in a sustained release manner over an extended drug delivery time period, comprising orally, subdermally or intramuscularly implanting a polymeric implant or a drug delivery system as disclosed herein into the subject. In some embodiments, the subject is afflicted with, susceptible to, or considered high risk for a communicable disease. In some aspects, the communicable disease is a human immunodeficiency virus (HIV).

Provided herein are methods for the prevention or treatment of a human immunodeficiency virus (HIV), the methods comprising orally, subdermally or intramuscularly implanting the polymeric implants or drug delivery systems disclosed herein into a subject in need thereof.

Provided herein are kits comprising the polymeric implants or drug delivery systems disclosed herein for the prevention or treatment of a communicable disease in a subject, and instructions for the use thereof. In some aspects, the communicable disease is a human immunodeficiency virus (HIV).

These and other embodiments are achieved in whole or in part by the presently disclosed subject matter. Further, embodiments of the presently disclosed subject matter having been stated above, other objects and advantages of the presently disclosed subject matter will become apparent to those skilled in the art after a study of the following description, Drawings and Examples.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, can be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

Like numbers refer to like elements throughout. In the figures, the thickness of certain lines, layers, components, elements or features can be exaggerated for clarity. Where used, broken lines illustrate optional features or operations unless specified otherwise. For a more complete understanding of the presently disclosed subject matter, reference is now made to the below drawings.

FIG. 1A) Placebo solution formulation prepared by dissolving PLGA in NMP at 1:2 w/w ratio (1), injecting the placebo solution into PBS (2), and incubating for 24 h (3) to allow depot formation and solidification. FIG. 1B) The resulting PLGA solid depot after 24-h incubation at 37° C.

FIGS. 1C and 1D) The resulting PLGA solid depots via incubation at varying times within microdialysis cassettes.

FIG. 2A) The specific surface area was determined based on implant weight and dimensions (i.e. volume) (n=4). FIG. 2B) Effect of PLGA solid implant shape on in vitro release kinetics of DTG. PLGA solid implants with different shapes were incubated over 140 days at 37° C. in 0.01M PBS (pH 7.4) with 2% solutol. PLGA implant (~25 mg) contained ~10% w/w of DTG. All error bars represent standard deviation for n=4. Graph inset represents the enlarged release kinetics of DTG for the initial 2 weeks phase. Varying shape of the implant directly affects the release kinetics of DTG from the implant. FIG. 2C) Images of the DTG-loaded PLGA implants before and after completed in vitro release study. Increase in the specific surface area over the study time was observed in all PLGA implants. FIG. 2D) SEM images representing cross-section images of the DTG-loaded PLGA implants of various shapes post incubation in PBS at 37° C. for 8, 12, and 16 weeks.

FIG. 9A) Fabrication process of PLGA solid tablets by phase inversion and direct compression techniques in a lab scale and a potential commercial manufacturing scale. FIG. 9B) DSC chromatograms of DTG, PSI placebo, and DTG loaded PSI. FIG. 9C) In vitro release profile of DTG from PLGA solid tablets fabricated by 1) a combination of phase inversion of DTG-loaded 1:6 PLGA/(NMP:DMSO) and direct compression process (compression force at 1 US.ton), and 2) a direct compression process of PLGA powder from phase inversion and DTG powder (compression force at 1 US.ton). Tablets were incubated at 37° C. in 0.01M PBS (pH 7.4 with 2% solutol) and data collected over 35 days (last timepoint collected, ongoing studies). Error bars represent standard deviation of n=3 samples.

FIG. 15A) Fracture strength of solid tablets with a 35 N load cell, displacement rate at 0.05 mm/s until rupture was observed for the solid implants. FIG. 15B) Young's modulus of solid tablets calculated from the compression test stress/strain graphs.

FIG. 19A) DTG concentration in dry solid PLGA tablets fabricated with 1:6 w/w PLGA/(NMP: DMSO) before, and after storage at 40° C. and 75% RH at 14, 30, 90, and 120 days. FIG. 19B) Physical appearance of DTG-loaded PSIs before and after storage for 40° C. and 75% RH for 14, 30, 90, and 120 days. FIG. 19C) HPLC chromatograms of DTG in solid PLGA tablets fabricated with 1:6 w/w PLGA/(NMP:DMSO) before, and after storage at 40° C. and 75% RH for 14, 30, 90, and 120 days.

FIG. 20A) Drug XRD patterns for DTG-loaded, RPV-loaded, or co-formulated DTG-RPV PSIs compared to their neat drug analogues. FIG. 20B) DSC thermograms comparing drug endotherms of DTG-loaded, RPV-loaded, or co-formulated DTG-RPV PSIs to neat drugs and placebo PSI.

FIG. 21A) Plasma concentration of DTG in BALB/c mice (n=5 per timepoint) administered with 10 mg of DTG PSI subcutaneously (~6 mg DTG) or 20 mg of DTG/RPV PSI (~6 mg DTG; ~6 mg RPV), FIG. 21B) In vitro concentration of DTG in 200 mL of release media (PBS pH7.4 with 2% of Solutol), FIG. 21C) Mouse plasma concentration of RPV (n=5 per timepoint) administered with 10 mg of RPV PSI subcutaneously (~6 mg of RPV) or 20 mg of DTG/RPV PSI (6 mg of RPV; ~6 mg DTG), FIG. 21D) In vitro concentration of RPV in 200 mL of release media (PBS pH7.4 with 2% of Solutol).

DETAILED DESCRIPTION

Figure 1A:
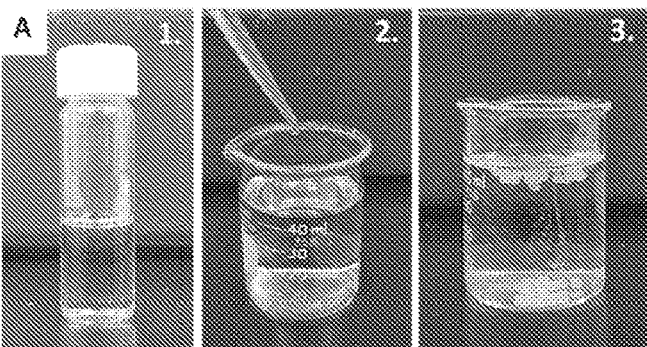
FIGS. 1A-1D. Formation of in-situ solid depots via phase inversion.

In the following detailed description, embodiments of the present inventive concept are described in detail to inform practice of the inventive concept. Although the invention is described with reference to these specific embodiments, it should be appreciated that the inventive concept can be embodied in different forms and should not be construed as limited to the embodiments set forth herein. Rather, these embodiments are provided so that this disclosure will be thorough and complete, and will fully convey the scope of the invention to those skilled in the art. All publications cited herein are incorporated by reference in their entireties for their teachings.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one skilled in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the present disclosure and the claims.

All publications, patent applications, patents and other references cited herein are incorporated by reference in their entireties for the teachings relevant to the sentence and/or paragraph in which the reference is presented.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of a composition, mass, weight, temperature, time, volume, concentration, percentage, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

As used herein, the term "substantially," when referring to a value, an activity, or to an amount of a composition, mass, weight, temperature, time, volume, concentration, percentage, etc., is meant to encompass variations of in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed apparatuses and devices. For example, a media or environment is "substantially hypoxic" when it is at least 60%, or at least 75%, or at least 80%, or at least 85%, or at least 90%, or at least 95%, and, in certain cases, at least 99%.

As used herein a "communicable disease" refers to an infectious condition that is transmitted from one person to another through a variety of ways that may include contact with blood and bodily fluids, breathing in an airborne virus, or by being bitten by an insect.

As used herein "HIV" generally denotes a human immunodeficiency virus. "HIV disease" is generally composed of several stages including the acute HIV infection, which often manifests as a flu-like infection and the early and medium stage symptomatic disease, which may include several non-characteristic symptoms such as skin rashes, fatigue, night sweats, slight weight loss, mouth ulcers, and fungal skin and nail infections. Most individuals infected with HIV will experience mild symptoms such as these before developing more serious illnesses. As HIV disease progresses, some individuals may become quite ill even if they have not yet been diagnosed with AIDS, the late stage of HIV disease. Typical problems include chronic oral or vaginal thrush (a fungal rash or spots), recurrent herpes blisters on the mouth (cold sores) or genitals, ongoing fevers, persistent diarrhea, and significant weight loss. "AIDS" is the late stage HIV disease and is a condition, which progressively reduces the effectiveness of the immune system and leaves individuals susceptible to opportunistic infections and tumors.

As used herein, the term "antiretroviral" as applied to a pharmaceutically active agent, drug, preparation, composition or the like refers to an agent, preparation, composition or the like that controls or inhibits the proliferation or multiplication of a retrovirus in a host that is susceptible to the retrovirus.

"Antiretroviral therapy" (ART) or "antiretroviral drug" may be used interchangeably herein to refer to a nucleoside reverse transcriptase inhibitor, an entry inhibitor, an integrase inhibitor, a fusion inhibitor, a protease inhibitor, and/or a non-nucleoside reverse transcriptase inhibitor also known as Combination antiretroviral therapy (cART) or Highly Active Antiretroviral Therapy or (HAART). Such antiretroviral therapy regimens include, but are not limited to, one or a combination of the following drugs: COMBIVIR® (lamivudine and zidovudine), EMTRIVA® (FTC, emtricitabine), EPIVIR® (lamivudine, 3TC), HMD® (zalcitabine, ddC, dideoxycitidine), RETROVIR® (zidovudine, AZT, azidothymidine, ZDV), TRIZIVIR® (abacavir, zidovudine, lamivudine), VIDEX® (didanosine, ddl, dideoxyinosine), VIDEX® EC (enteric coated didanosine), VIREAD® (tenofovir disoproxil fumarate), ZERIT® (stavudine, d4T), ZIAGEN® (abacavir), AGENERASE® (amprenavir), CRIXIVAN® (indinavir, IDV, MK-639), FORTOVASE® (saquinavir), INVIRASE® (saquinavir mesylate, SQV), KALETRA® (lopinavir and ritonavir), NORVIR® (ritonavir, ABT-538), REYATAZ® (atazanavir sulfate), VIRACEPT® (nelfinavir mesylate, NFV), FUZEON® (enfuvirtide, T-20), RESCRIPTOR® (delavirdine, DLV), SUSTIVA® (efavirenz) and VIRAMUNE® (nevirapine, BI-RG-587).

The term "prevent," "preventing" or "prevention of" (and grammatical variations thereof) refers to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression are less than what would occur in the absence of carrying out the steps of the methods of the present invention.

Also as used herein, the terms "treat," "treating" or "treatment" may refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, delay of the onset of the disease, disorder, or illness, and/or change in clinical parameters of the condition, disorder, disease or illness, etc., as would be well known in the art.

A "therapeutically effective amount," "treatment effective amount" and "effective amount" as used herein are synonymous unless otherwise indicated, and mean an amount of a pharmaceutical agent, composition or formulation that is sufficient to improve the condition, disease, or disorder being treated and/or achieved the desired benefit or goals as described herein. Those skilled in the art will appreciate that the therapeutic effects need not be complete or curative, as long as some benefit is provided to the subject. Similarly, a "prevention effective" amount as used herein is an amount that is sufficient to prevent (as defined herein) the disease, disorder and/or clinical symptom in the subject. Those skilled in the art will appreciate that the level of prevention need not be complete, as long as some benefit is provided to the subject.

As used herein, a subject is "high risk" or has an "increased likelihood" of some clinical feature or outcome (e.g., contraction, recurrence or progression) if the probability of the subject having the feature or outcome exceeds some reference probability or value. The reference probability may be the probability of the feature or outcome across the general relevant subject or patient population. For example, if the probability of contracting a communicable disease in the general population is X and a particular patient has been determined to have a probability of contracting a communicable disease of Y and if Y>X, then the patient has a "high risk" or "increased likelihood" of contracting a communicable disease. Alternatively, a threshold or reference value may be determined and a particular patient's probability of contracting a communicable disease may be compared to that threshold or reference. Further, as noted by the Centers for Disease Control and Prevention, anyone can be affected by a communicable disease regardless of sexual orientation, race, ethnicity, gender or age. However, certain groups are at higher risk communicable diseases (e.g., HIV) because of particular risk factors. For example, a subject may be "high risk" or has an "increased likelihood" of contracting a communicable disease in view of a particular lifestyle, status of partners, risk behaviors, and communities where the subject lives.

The present inventive concept provides polymeric implants and controlled release drug delivery systems to provide high drug loading and long-acting drug release. Moreover, the polymeric implants and controlled release drug delivery systems may be developed using relatively simple, scalable and/or cost-effective techniques. The polymeric implants and controlled release drug delivery systems may accommodate one or more antiretroviral drugs at concentrations translatable to a human dose, provide long-acting drug release over >30 days, and/or be readily removed from the body.

Specifically, embodiments of the present disclosure include a method of making a polymeric implant comprising forming a homogeneous drug-loaded polymer wherein forming the homogenous drug-loaded polymer comprises utilizing a phase inversion technique comprising introducing a solution comprising (a) a biodegradable polymer, (b) a water miscible biocompatible organic solvent, (c) at least one pharmaceutically active agent, and optionally (d) release rate-limiting additives (e.g. PLA, PCL, PEG, pluronics, SAIB) to an aqueous medium wherein the solvent diffuses into the aqueous medium during phase inversion providing an insoluble solid composition comprising the pharmaceutically active agent and the polymer; micronizing the insoluble solid composition; and utilizing direct compression of the micronized insoluble solid composition to form a solid tablet. The solid tablet may have a range of shapes and sizes (e.g., round, rod, sphere, square, star, Y-shape, T-shape, U-shape) forming the polymeric implant. In particular embodiments, the flexibility of fabricating solid tablets with a range of sizes and shapes is particularly important to optimize drug dose requirements, patient compliance, and/or efficacy outcomes.

In particular embodiments, the biodegradable polymer is selected from the group consisting of, but not limited to, poly (lactic-co-glycolic acid) (PLGA), poly (lactic acid) (PLA), poly (glycolic acid) (PGA), polycaprolactone (PCL), sucrose acetate isobutyrate (SAIB), cellulose. In further embodiments, the biodegradable polymer is poly (lactic-co-glycolic acid) (PLGA). In some embodiments, the water miscible biocompatible organic solvent is selected from the group consisting of, but not limited to, N-methyl-2-pyrrolidone (NMP), dimethyl sulfoxide (DMSO), Gelucire®, Tween®, Labrasol®, acetone, methanol. In some embodiments, the water miscible biocompatible organic solvent can be a combination of two solvents, e.g. NMP and Gelucire® or a combination of a solvent with a surfactant, e.g. NMP and Brij® 78 or NMP and Vitamin E TPGS. In particular embodiments, the ratio of biodegradable polymer to water miscible biocompatible organic solvent is from 1:2, 1:4, 1:6, 1:8, or 1:10. In still other embodiments, the ratio of biodegradable polymer to water miscible biocompatible organic solvent is 1:2, 1:4 or 1:6 and not higher than 1:10 so as to maintain a desirable structural integrity.

According to embodiments of the present disclosure, the at least one pharmaceutically active agent is selected from the group consisting of an analgesic agent; an anti-anxiety agent; an anti-arthritic agent; an anti-asthmatic agent; an anticancer agent; an anticholinergic agent; an anticholinesterase; an anticonvulsant; an antidepressant; an antidiabetic agent; an antidiarrheal agent; an anti-emetic agent; an antihistamine; an antihyperlipidemic agent; an anti-infective agent; an anti-inflammatory agent; an antimigraine agent; an anti-obesity agent; an antipruritic agent; an antipsychotic agent; an antiretroviral agent, an antispasmodic agent; an agent for treating a neurodegenerative disease; a cardiovascular medicament; contraceptive agent, a diuretic agent; a gastrointestinal medication; a hormone or anti-hormone; a hypnotic agent; an immunosuppressive agent; a leukotriene inhibitor; a narcotic agonist or antagonist; a neurotransmitter; a nucleic acid; a nutrient; a peptide drug; a protein, an antibody, a nutrient; a sympathomimetic agent; a thrombolytic agent; a vasodilator; or a combination thereof. In some embodiments, the at least one pharmaceutically active agent is at least one antiretroviral agent. In others, the at least one pharmaceutically active agent is a combination of at least two drugs. That is, a combination of drug agents may be delivered to a subject using the present inventive concept. In particular embodiments, at least one drug is an antiretroviral agent. In some embodiments, at least one drug comprises a contraceptive agent, e.g., Ethinyl Estradiol, Levonorgestrel, Desogestrel, Norethindrone, Progesterone, β-Estradiol. In further embodiments, the combination of drug agents is a combination including an antiretroviral agent and a contraceptive agent where, in some embodiments, there can be more than one type of each included in the implant of the present disclosure.

Unexpectedly, the present disclosure provides a method of forming a solid implant that can be formed into a tablet having various shapes and sizes. In some embodiments, the tablet is in the shape of a rod, a square, a sphere, a disk, a star, a round shape, Y-shape, T-shape, U-shape or an undefined shape. The ability to form different shapes and sizes has a positive effect on drug release rates as shown in the examples below. Moreover, the ability to form various shapes of the implant may have a significant effect on patient comfort and ultimately, patient compliance. Moreover, the compression technology to form solid implants allows engineering of smaller implants with high drug loading to achieve drug dose requirements. Current solid implant technologies require the use of multiple implants to increase drug dose. In some cases, the use of solid implants is not possible because their size will be too large to meet drug dose requirements.

According to additional embodiments of the present disclosure, a polymeric implant formed according to the methods described above is provided. The polymeric implant is a solvent-free polymeric implant. Moreover, the polymeric implant is biodegradable, yet maintains a desirable amount of structural support and mechanical properties resisting mechanical fail such as dissection, tear, shear, rip, compression etc. during the period of degradation.

Embodiments of the present disclosure also provide a controlled release drug delivery system comprising an implantable device that provides controlled release of at least one pharmaceutically active agent throughout an extended drug delivery time period, the implantable device comprising a drug-loaded polymer formed by a process comprising utilizing a phase inversion technique comprising introducing a solution comprising (a) a biodegradable polymer, (b) a water miscible biocompatible organic solvent, (c) at least one pharmaceutically active agent, and optionally (d) a release rate-limiting agent to an aqueous medium wherein the solvent diffuses into the aqueous medium during phase inversion to provide an insoluble solid composition comprising the pharmaceutically active agent and the polymer; micronizing the insoluble solid composition; and utilizing direct compression of the micronized insoluble solid composition to form the implantable device, wherein following implantation of the device into a subject, the implantable device results in a serum level of the pharmaceutically active agent sufficient to achieve therapeutic efficacy during the extended drug delivery time period.

In some embodiments, the insoluble solid composition comprising the pharmaceutically active agent and the polymer is formed in situ. In still other embodiments, the pharmacologically active agent is released at a rate that is substantially constant throughout the effective drug delivery time period. In some embodiments, the effective drug delivery time period is in the range of about one month to about four years, and in others, the effective drug delivery time period is in the range of about one month to about 1 year.

In some embodiments, the subject is afflicted with, susceptible to, or considered high risk for a communicable disease. In further embodiments, the communicable disease is a human immunodeficiency virus (HIV).

Embodiments of the present disclosure also provide a method for administering a pharmacologically active agent to a subject in a sustained release manner over an extended drug delivery time period, comprising orally, subdermally or intramuscularly implanting the polymeric implant or the drug delivery system described herein into the subject. The subject may be afflicted with, susceptible to, or considered high risk for a communicable disease. The communicable disease may be a human immunodeficiency virus (HIV).

Embodiments of the present disclosure further provide a method for the prevention or treatment of a human immunodeficiency virus (HIV), the method comprising orally, subdermally or intramuscularly implanting the polymeric implant or the drug delivery system described herein into a subject in need thereof.

Additionally, embodiments of the present disclosure provide a kit comprising the polymeric implant or the drug delivery system described herein for the prevention or treatment of a communicable disease in a subject, and instructions for the use thereof.

Subjects suitable to be treated by the methods of the present invention include, but are not limited to mammalian subjects. Mammals according to the present invention include, but are not limited to, canines, felines, bovines, caprines, equines, ovines, porcines, rodents (e.g., rats and mice), lagomorphs, primates, humans and the like, and mammals in utero. Any mammalian subject in need of being treated or desiring treatment according to the present invention is suitable. Human subjects of any gender (for example, male, female or transgender) and at any stage of development (i.e., neonate, infant, juvenile, adolescent, adult, elderly) may be treated according to the present invention. Subjects may be of any race or ethnicity, including, but not limited to, Caucasian, African-American, African, Asian, Hispanic, Indian, etc., and combinations thereof. It should be further noted that subject and patient are used interchangeably.

In particular embodiments, the subject has never been diagnosed with or suffered from a communicable disease. In other embodiments, the subject may be diagnosed with, afflicted with, suffering from or at risk for a communicable disease. In some embodiments, the subject has previously undergone treatment for a communicable disease. In other embodiments, the subject may be in remission from a communicable disease. In other embodiments, the subject may be one where contraception is desired. In some embodiments, the communicable disease is HIV.

The present invention is more particularly described in the following illustrative examples that are intended as illustrative only since numerous modifications and variations therein will be apparent and understood to those skilled in the art.

EXAMPLES

The following examples are included to demonstrate embodiments of the present disclosure. It should be appreciated by those of skill in the art that the techniques disclosed in the examples, in light of the present disclosure, can be modified or changed and still obtain a like or similar result without departing from the spirit and scope of the present disclosure.

Example 1

Materials and Methods

Preparation of In-Situ PLGA-Based Solid Depots by Phase Inversion

The solvent-depleted depots were prepared by a three-step protocol using a phase inversion technique. (1) Placebo formulation: 50:50 Poly(DL-lactide-co-glycolide) (PLGA), MW 27 kDa, was mixed with N-methyl-2-pyrrolidone (NMP) at various weight ratios of PLGA/NMP (w/w) and allowed to dissolve by continuous mixing at room temperature (Placebo). To assess the effect of PLGA/NMP ratio on a) drug loading capacity, b) drug entrapment, c) macro-/microstructures, and d) release kinetics, placebo formulations containing 1:2, 1:4 and 1:6 w/w ratios of PLGA/NMP were prepared. (2) Drug loading: Dolutegravir (DTG) was subsequently added to the PLGA/NMP placebo solution at its maximum concentration in the formulation and was allowed to stir at 37° C. overnight to dissolve the drug. (3) Depot formation: A sample from the resulting drug-loaded formulation (25 μL, 20±3 mg) was injected into 15 mL of 0.01 M PBS pH 7.4 using a pipette and incubated at 37° C. for 24 h to produce a spherical solid implant. To assess the effect of implant shape on release kinetics, rod, sphere, and square shaped implants were fabricated. The rod and square shaped depots were fabricated by injecting the drug loaded formulation into a micro-dialysis tube and micro-dialysis cassette, respectively, before incubating into 15 mL of PBS at 37° C. for 24 h. To assess the effect of co-solvent in the formulations on drug loading capacity, drug entrapment, and release kinetics, co-solvent systems containing 9:1 w/w ratio of NMP/dimethyl sulfoxide (DMSO), and NMP/Gelucire 44/14 were prepared. Each co-solvent system was then mixed with PLGA at 1:6 w/w ratio of PLGA/Co-solvent to make placebo solutions. Dolutegravir (DTG) was added to the placebo formulation at the maximum concentration and allowed to dissolve in the solution following the aforementioned procedure above. Solid spherical implants were prepared using the aforementioned procedure by phase inversion following injection of DTG/PLGA/solvent solution into an aqueous medium at 37° C.

Figure 8:
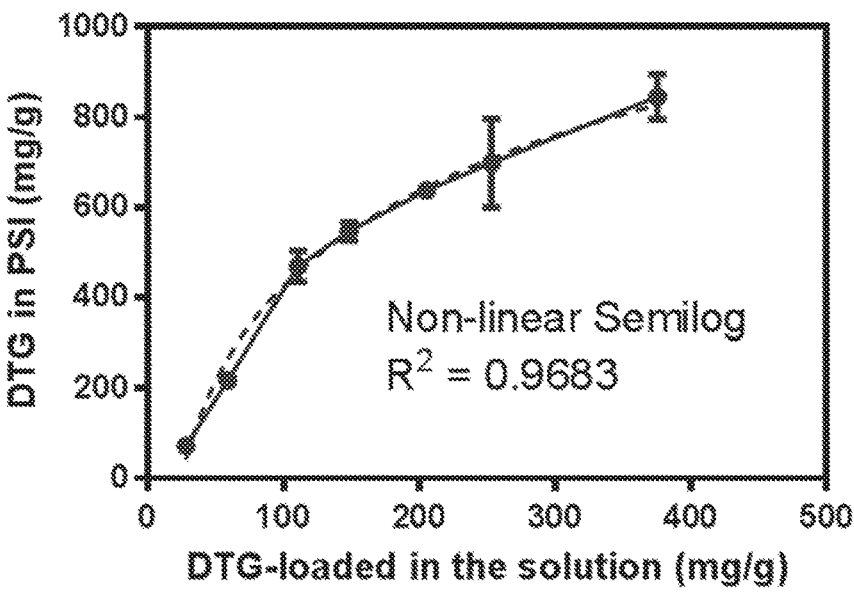
FIG. 8. Interpolation of DTG final concentration in PSIs based on the original loading concentration of DTG in a 1:6 w/w PLGA:(NMP/DMSO 9:1 w/w) solution.

Preparation of PLGA Solid Tablets by Direct Compression of Micronized In-Situ PLGA Depots To fabricate a solvent-depleted DTG-loaded PLGA solid tablet, there are three simple scalable steps required: 1) forming in-situ DTG-loaded polymer solids by phase inversion technique following the protocol mentioned above; 2) drying the DTG-loaded PLGA solids using a rotary evaporator for 1 h to remove any residual volatile solvent, and micronizing the dry solids to obtain a fine powder using a mortar and pestle; and 3) tablet compressing of the micronized DTG-loaded PLGA powders using a single punch press tablet machine (Carver Hand Press model 3851). Briefly, 75 mg of DTG-loaded PLGA powder was loaded into a 10-mm dimeter cylindrical tool and pressed at a 1 US.ton compression force (1.274 US.ton/cm$^2$) for 10 s at room temperature. Before direct compression, the uniformity and homogeneity of DTG distribution within the micronized PLGA powder was determined by HPLC analysis. No additives were used to form the tablet and the final tablet contained only PLGA, DTG and any residual non-volatile solvent (e.g. Gelucire®). The drug loading in the solid implants can be adjusted to achieve a wide range of drug concentrations (e.g. about 7% w/w to about 84.5% w/w) to meet desired drug dose based on the amount of drug loading in the polymer/solvent solution. The final drug concentration in the solid implant can be determined from a non-linear semi-logarithmic plot (FIG. 8).

To assess the effect of tablet compression force on the mechanical properties of the tablet and the release kinetics of DTG, formulations containing 1:6 w/w ratios of PLGA/(NMP:DMSO (9:1 w/w)) were prepared. Dolutegravir (DTG) was subsequently added to the PLGA placebo solution at its saturation concentration of 250 mg/g and stirred at 37° C. overnight to dissolve the drug. The resulting drug-loaded solution was injected into 0.01 M PBS pH 7.4 using a pipette and incubated at 37° C. for 24 h to produce a PLGA/drug solid depot. The PLGA/drug depot (75 mg) was dried using a rotary evaporator to remove residual volatile solvent, micronized, loaded into a 10-mm cylindrical tool and compressed at different compression forces of 0.5, 1, and 1.5 US. Ton (equal to 0.657, 1.274, 1.911 US.ton/cm$^2$, respectively) to produce tablets. The resulting tablets were tested for their mechanical properties and in vitro release kinetics of DTG following the protocol mentioned below.

Drug Loading Study

The saturation concentration of DTG in formulations containing 1:2, 1:4 and 1:6 w/w ratios of PLGA/NMP was determined. 30 mg of DTG was added to individual vials containing 100 mg of PLGA/NMP. The mixture was mixed thoroughly using a vortex with short-warming for several cycles, and stirred at 37° C. for 24 h. Samples were subsequently centrifuged for 30 min at 13,000 rpm (Eppendorf Centrifuge 5417C, USA) to remove excess undissolved drug. Sample aliquots (1 mg, n=4) were collected from the saturated supernatant and diluted with acetonitrile (ACN). Drug concentration in the saturated aliquots was determined by HPLC analysis.

A reverse-phase HPLC analysis was carried out with a Finnigan Surveyor HPLC system (Thermo Finnigan, San Jose, California, USA) with a Photodiode Array (PDA) Plus Detector, auto-sampler, and LC Pump Plus. The stationary phase utilized for the analysis was an Inertsil ODS-3 column (4 μm, 4.6 Å~150 mm, [GL Sciences, Torrance, CA]) maintained at 40° C. Chromatographic separation was achieved by gradient elution using a mobile phase consisting of 0.1% trifluoroacetic acid in water and ACN (H$_2$O/ACN 95:5 v/v). The flow rate was 1.0 mL/min and the total run time was 25 min for each 25 μL injection.

Drug Entrapment Study

DTG was loaded to the PLGA/NMP solutions at the maximum loading concentrations ($C_{loaded}$) and subsequently produced spherical solvent-free implants. After solidifying for 24 h in 15 mL of 0.01 M PBS pH 7.4 at 37° C., the content of DTG entrapped in formulations containing 1:2, 1:4 and 1:6 w/w ratios of PLGA/NMP was determined. Sample aliquots (1 mL) from the release medium were collected and analyzed by the HPLC method described above to quantify the concentration of unentrapped DTG in the supernatants ($C_{free}$). The percent DTG entrapment in the solidified formulations was then calculated following the formula below. All experiments were performed in quadruplicate.

$$\% \ DTG \ \text{entrapment} = \frac{C_{loaded} - C_{free}}{C_{loaded}} \times 100$$

Differential Scanning Calorimetry (DSC) Analysis of Drug-Loaded PSIs

DSC analysis for drug neat (DTG and RPV), PSI placebos, and drug-loaded PSIs (DTG, RPV, co-formulated DTG-RPV) was carried out using a differential scanning calorimeter (TA Q200, USA). Samples (range in 3-10 mg) were weighed, hermetically sealed in an aluminum pan, and placed in the differential scanning calorimeter. Samples were subsequently heated from 0-250° C. for DTG formulations, and 0-300° C. for RPV formulations at a heating rate of 10° C./min, under nitrogen atmosphere (flow rate 20 mL/min). The thermograms were used to determine the peak glass transition temperature ($T_g$).

X-Ray Powder Diffraction (XRD) Analysis

Powder x-ray diffraction (XRD) data was collected on Rigaku SmartLab system with a Cu source operated at 40 kV and 44 mA. A Kβ filter was used to remove the Kβ line from the Cu source. Data was collected in a Bragg Brentano geometry with the HyPix detector operated in 1D mode. Scans were acquired at 5 degrees/min with a step size of 0.01 degrees.

In Vitro Drug Release Studies

Drug release kinetics from various implant formulations was evaluated by incubating solid implants (25 mg±5 mg) into 200 mL of release medium (0.01 M PBS pH 7.4 with 2% solutol HS) at 37° C. for greater than 7 months. Sample aliquots (1 mL) were collected at various time points and replaced with fresh release medium. The release medium was completely removed and replaced with fresh medium every week to maintain sink conditions. The DTG concentration in the release samples was quantified by HPLC using the method described above. Cumulative drug release was calculated from the HPLC analysis and normalized to the total mass of drug in the implant. All experiments were performed in quadruplicate.

DTG release kinetics of solid tablets was assessed by incubating the tablets (75 mg±0.5 mg) in 500 mL of release medium (0.01 M PBS pH 7.4 with 2% solutol HS), and at 37° C. for up to 6 months. Sample aliquots (1 mL) were collected and DTG concentration was quantified by HPLC following the procedure mentioned above.

Scanning Electron Microscopy (SEM) Imaging and Analysis

Microstructures of solid implants were evaluated by scanning electron microscopy (SEM). To investigate the effect of PLGA/NMP weight ratio on drug distributions and the microstructure of the depots, depots prepared by injecting formulation solutions (25 μL) containing DTG in varying weight ratios of PLGA/NMP (1:2, 1:4, 1:6, and 1:8 w/w PLGA/NMP) into 15 mL of PBS and incubating for 24 h at 37° C. The resulting solid depots were removed from the PBS, flash frozen with liquid nitrogen, and then lyophilized for 24 h (SP VirTis Advantage XL-70, Warminster, PA). The lyophilized samples were subsequently fractured and mounted on an aluminum stub using carbon tape, and sputter coated with 5 nm of gold-palladium alloy (60:40) (Hummer X Sputter Coater, Anatech USA, Union City, CA). The coated samples were imaged using a Zeiss Supra 25 field emission scanning electron microscope with an acceleration voltage of 5 kV, 30 μm aperture, and average working distance of 15 mm (Carl Zeiss Microscopy, LLC, Thornwood, NY).

Accelerated Stability Test

The selected implant formulations with DTG were tested for long-term stability under accelerated conditions. The solid implants were stored in a desiccator and maintained at 40° C./75% relative humidity (RH) in a Fisher Scientific Isotemp Incubator (Pittsburgh, Pa.). Depot samples were collected at various intervals (0, 7, 14 days, 1 month), and analyzed by HPLC for drug content and presence of any degradation products. Zero-time samples were used as controls (i.e. 100% DTG concentration).

Mechanical Strength of PLGA Solid Tablets

To evaluate the mechanical properties of the PLGA solid tablets, a three-point bending test was performed on a RSAIII micro-strain analyzer (TA Instruments, USA) fitted with three-point bending geometries. For each measurement, a PLGA solid tablet (10-mm outer diameter) was placed on the lower 3-point bending tool, and the sample was then tested with a 35 N load cell at a strain rate of 0.05 mm/s until rapture was observed from the tablets.

In Vivo Pharmacokinetic Studies.

All in vivo studies were performed in BALB/c mice. Eight-week (20-25 g) female BALB/c mice were purchased from The Jackson Laboratory (Bar Harbor, Me.). The procedures were performed in accordance with the guidelines for animal experimentation by the Institutional Animal Care and Use Committee, School of Medicine, University of North Carolina at Chapel Hill.

DTG-loaded PSI (280 mg/kg; 10 mg PSI tablet), RPV-loaded PSI (290 mg/kg; 10 mg PSI tablet), sandwiched DTG/RPV-loaded PSI tablet (280 and 290 mg/kg of DTG and RPV; 20 mg PSI tablet), or a similar weight of placebo PSI tablet were administered subcutaneously via a 1-cm skin incision on a shaved back of anesthetized BALB/c mice (n=7 per group; 4 groups). The skin at the incision site was then closed with clinical grade Ethicon suture plus Vetbond between sutures or with 2-3 sterile 9 mm stainless steel wound clips.

Samples (plasma, vaginal lavage, cervico-vaginal tissues) were collected at 24 h and at days 3, 7, 14, 21, 30, 60, 90, 120, 150, and 180 (n=7 per time point). Peripheral blood was collected from mice into capillary tubes coated with or without EDTA to isolate plasma or serum, respectively. Cervico-vaginal secretions (CVS) were obtained by lavage with sterile PBS (three washes of 20 μl each, ~60 μl total volume). All samples were stored at −80° C. until analysis. Mice were monitored longitudinally for presence of drug in peripheral blood. Drug plasma concentration was quantified by protein precipitation and LC-MS/MS analysis. Calibration curves were obtained using a 1/concentration$^2$ weighted linear regression of analyte:internal standard peak area ratio versus nominal concentration. Compilation of concentration results and descriptive statistical analyses were performed using Sciex Analyst version 1.6.1. Ten microliters of each stored plasma sample was mixed with 30 μL of acetonitrile containing the isotopically labeled internal standard, DTG (DTG-IS) and RPV (RPV-IS). Following vigorous mixing and centrifugation, a portion of the supernatant was diluted with 50:50 methanol:water prior to LC-MS/MS analysis. Drug analyte was eluted from a Varian (Agilent) Pursuit Diphenyl (2.1×50 mm, 3 μm particle size) analytical column.

Example 2

In-Situ PLGA Solid Depot Formation by Phase Inversion Technique

Figure 1B:
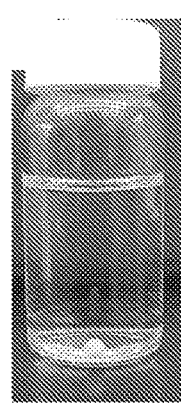

Solvent-free PLGA solid depots were successfully formed by phase inversion technique by direct injection into water (FIG. 1A) or by injection into a microdialysis membrane followed by incubation into water (FIG. 1B). Upon injection/incubation into water or PBS the water miscible bio-compatible solvent (e.g. NMP) diffuses out and the polymer (PLGA) and drug precipitate out to form a solid depot.

Figure 1C:
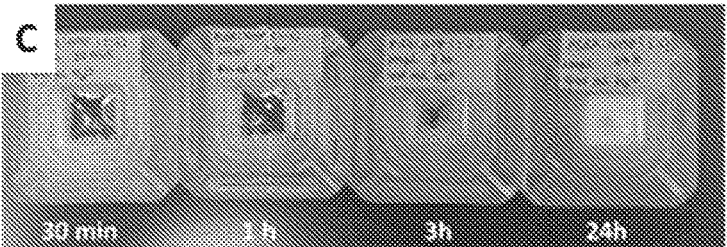
Figure 1D:
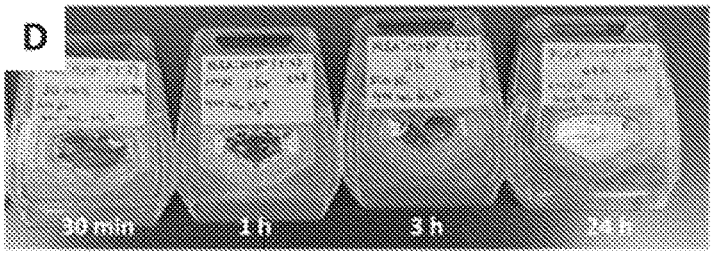

Using a microdialysis membrane, the shape and size of the PLGA/drug solid depot can be manipulated. Namely, the ISFI solution (0.1 mL) was injected into a microdialysis membrane (FIG. 1C-D) with a molecular weight cut-off (MWCO 10 kDa) lower than the molecular weight of PLGA polymer (PLGA 27 kDa). The dialysis membrane allowed the solvent to diffuse into the water and form a solid depot inside the membrane. A 24 h incubation time was found to be the optimum time to produce a solid depot via phase inversion of PLGA/drug. Using phase inversion technique, solid depots can be fabricated with one or more drugs by dissolving the drug(s) in the polymer solution at target concentrations.

Example 3

Figure 2A:
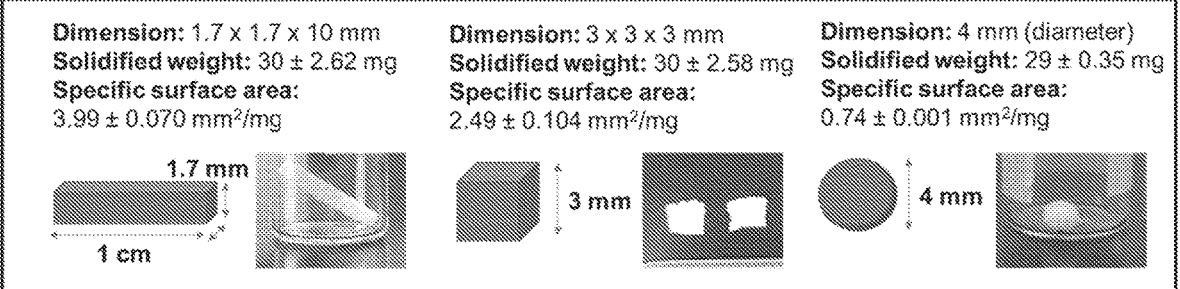
FIGS. 2A-2D. Illustration shows the optimized dimensions, solid weights, and specific surface areas of depots in different shapes (cuboid, cube and sphere) investigated in the in vitro release study.
Figure 2B:
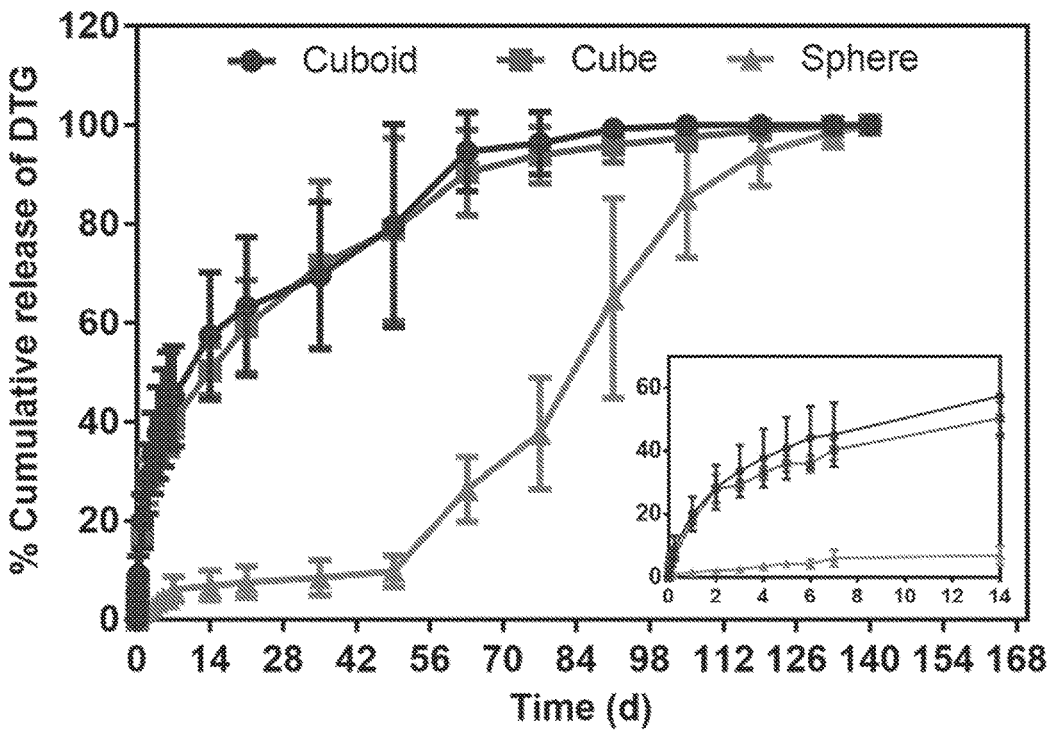
Figure 2C:
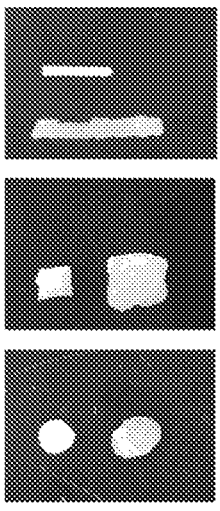
Figure 2D:
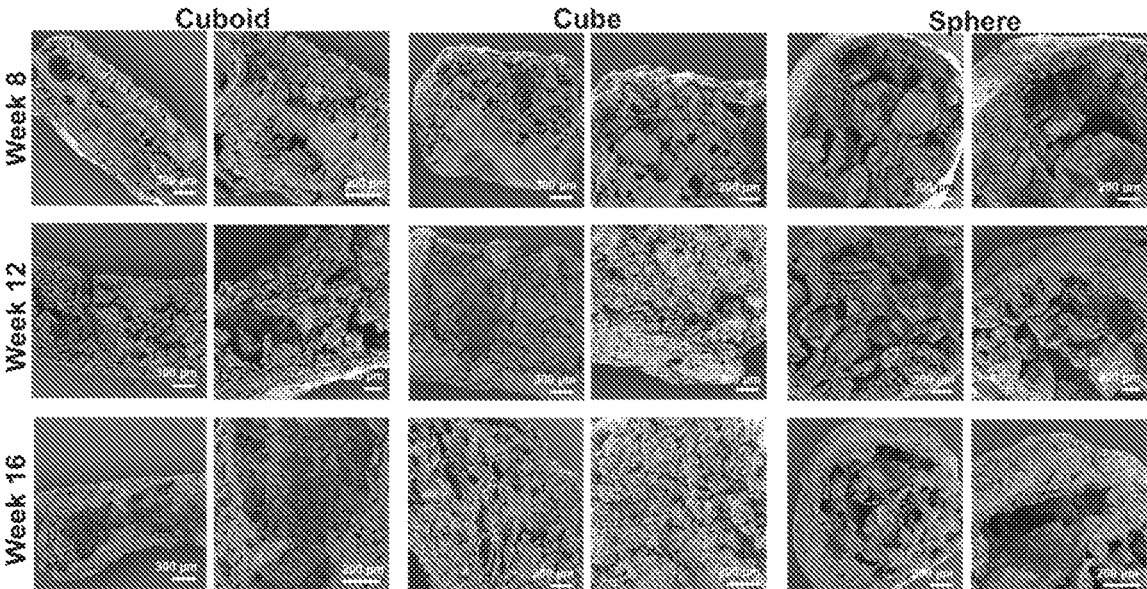

Prototype PLGA Solid Implants Fabricated with Different Shapes: Effect of Shape on Drug Release Kinetics Three implant shapes (rod, square, or sphere) were selected as prototype structures for studying the impact of implant shape on in vitro drug release kinetics. In this study, DTG was selected as a drug model for HIV PrEP as its well-known efficacy for HIV treatment. The formulations were prepared with constant drug concentration (DTG at 100 mg/mL), PLGA/NMP ratio (1:2 w/w), PLGA MW (27 kDa), and different implant shapes. The rod and square shapes were prepared using microdialysis tubes and cassettes respectively. The spherical shape was simply prepared by injecting the DTG-loaded PLGA solution into PBS using a pipette (FIGS. 1A-1B). Before initiating the in vitro release studies of DTG from these implants, the specific surface area of each implant shape was quantified based on their weights and dimensions. The results show that the rod-shaped solid depots exhibited the highest specific surface area (SSA), followed by square then sphere depots (n=4, Table 1 below). This research demonstrates that the shape of the solid implant had an effect, sometimes significant, on the release rates of DTG. These results showed that DTG release rate was higher with higher SSA with the spherical depots releasing the slowest and the rod-shaped implants releasing the fastest. Release of drug through the implant system initially occurs through diffusion, and there was no initial burst release observed for the spherical depots exhibiting the lowest SSA and slowest release kinetics (FIG. 2B). The implants with higher specific surface area (rod and square) exhibited greater burst release of DTG at early time points (24-48 h) compared to the spherical implants. After initial diffusion of drug into the media system, sustained release was achieved via degradation of the PLGA polymer (hydrolysis of ester linkages) in the presence of water. It was also shown that the swelling properties of the implants had an effect on the release rate of DTG at later time points beyond 4 weeks. The results herein demonstrate that the rod and square implants exhibited significant swelling after ~5 weeks while the sphere-shaped implants exhibited noticeable swelling after ~9 weeks resulting in increased release rates of DTG from the implants (FIG. 2B). It is important to note however that the volume used in the in vitro studies (200 mL) is much higher than the volume present in the in vivo subcutaneous environment. Therefore, the swelling properties observed in these solid implants in vitro may not be observed in vivo.

TABLE 1

| Implant Shape | Specific surface area (mm²/mg) |
|---|---|
| Rod | 3.99 ± 0.07 |
| Square | 2.49 ± 0.10 |
| Sphere | 0.74 ± 0.00 |

The specific surface areas of the DTG-loaded PLGA implants (~DTG 100 mg/g of depot) fabricated at varying shapes. The specific surface areas were quantified based on their weights and dimensions (n=4).

Example 4

Prototype PLGA Implants Fabricated by Varying Formulations Parameters: Effect on Drug Loading Capacity, Drug Entrapment, Implant Formation, Microstructure, Release Kinetics, and Stability The Effect of Ratio of PLGA:NMP.

In this study, formulations were prepared with five (5) different weight ratios of PLGA:NMP (1:2, 1:4, 1:6, 1:8, and 1:10 w/w) and a PLGA (50:50 LA/GA) MW of 27 kDa to investigate: a) maximum DTG loading concentration; b) entrapment efficiency of DTG in solid depots following in-situ phase inversion; c) their macro-/micro-morphologies and drug distribution; and d) DTG release profiles.

Effect of PLGA/NMP Weight Ratio on Drug Loading Capacity.

First, the impact of PLGA:NMP ratio on DTG solubility was investigated. It was predicted that the HIV PrEP target human dose requirement for DTG is ≥600 mg. In order to reach the target DTG dose in the formulation, various ratios of PLGA:NMP were tested to maximize solubility of DTG. The results show that 1:10 w/w ratio of PLGA:NMP provided the highest loading capacity of DTG at approximately 280 mg/mL, followed by 1:8, 1:6, 1:4, and 1:2 ratio of PLGA:NMP (Table 2 below).

TABLE 2

| Solvent system | DTG Loading capacity | |
|---|---|---|
| | w/w (mg/g) | w/v (mg/mL) |
| 1:2 PLGA:NMP | 112.94 ± 2.97 | 124.24 ± 3.27 |
| 1:4 PLGA:NMP | 174.83 ± 4.16 | 192.32 ± 4.57 |
| 1:6 PLGA:NMP | 210.81 ± 2.90 | 231.89 ± 3.19 |
| 1:8 PLGA:NMP | 217.88 ± 6.22 | 239.66 ± 6.84 |
| 1:10 PLGA:NMP | 256.80 ± 9.80 | 282.48 ± 10.78 |

Loading capacity of DTG in varying PLGA:NMP formulations (n = 4).

Effect of PLGA/NMP Weight Ratio on In-Situ Implant Formation.

Figure 3:
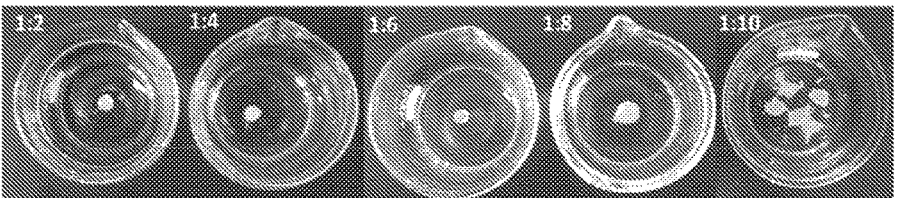
FIG. 3. Structures of solid PLGA implants fabricated with ISFI solutions containing varying PLGA:NMP ratios (n=4) via a 24-h incubation in PBS (pH 7.4) at 37° C. Ratios of PLGA/NMP greater than 1:8 w/w cannot form stable solid depots.

The structure integrity of the solid implant is highly important for its manufacturing process and its applications for controlled drug delivery. The morphology of solid PLGA implant was investigated using a range of PLGA:NMP ratios. It was found that PLGA solutions prepared with PLGA:NMP ratios of 1:2, 1:4 and 1:6 were able to form a rigid spherical structure after 24-h incubation in PBS at 37° C. However, the formulation containing 1:8 and 1:10 ratios of PLGA/NMP formed brittle thin flat solids after a 24-h incubation in PBS at 37° C., particularly for the 1:10 PLGA/NMP ratio (FIG. 3).

Effect of PLGA/NMP Ratio on Drug Entrapment.

Based on the aforementioned results, formulations containing PLGA/NMP ratios of 1:2, 1:4, 1:6, and 1:8 were selected to investigate the effect of PLGA:NMP ratios on drug entrapment. During the phase inversion process, when the NMP solvent diffuses out, a small amount of drug also diffused out from the polymer matrix. Therefore, it was important to determine the drug entrapment efficiency in the solid implant post phase inversion. In this study, formulations containing varying weight ratios of PLGA:NMP were prepared with maximum DTG concentration in each formulation. The solid implants were formed by injecting formulation solutions into 15 mL of 0.01M PBS (pH 7.4) using a pipette. The percent drug entrapment in the solid implants was quantified by subtracting the amount of drug that diffused out during phase inversion from the original amount of drug loaded. Based on the result in Table 3 (below), the percent entrapment of DTG in all formulations was ~90% or greater and higher entrapment was obtained with formulations containing higher PLGA/NMP ratios. This can be explained by the fact that higher PLGA/NMP ratios resulted in a faster phase inversion process and therefore greater DTG entrapment.

TABLE 3

| Implant formulation | Drug entrapment (%) |
|---|---|
| 1:2 PLGA:NMP | 89.87 ± 1.58 |
| 1:4 PLGA:NMP | 91.51 ± 1.13 |
| 1:6 PLGA:NMP | 92.31 ± 0.50 |
| 1:8 PLGA:NMP | 95.96 ± 0.28 |

Percent entrapment of DTG in solid implants (n=4) fabricated with varying PLGA:NMP ratios post incubation in 15 mL of 0.01M PBS (pH 7.4) at 37° C. for 24 h.

Effect of PLGA/NMP Weight Ratio on the Microstructure of Solid Implants.

Figure 4:
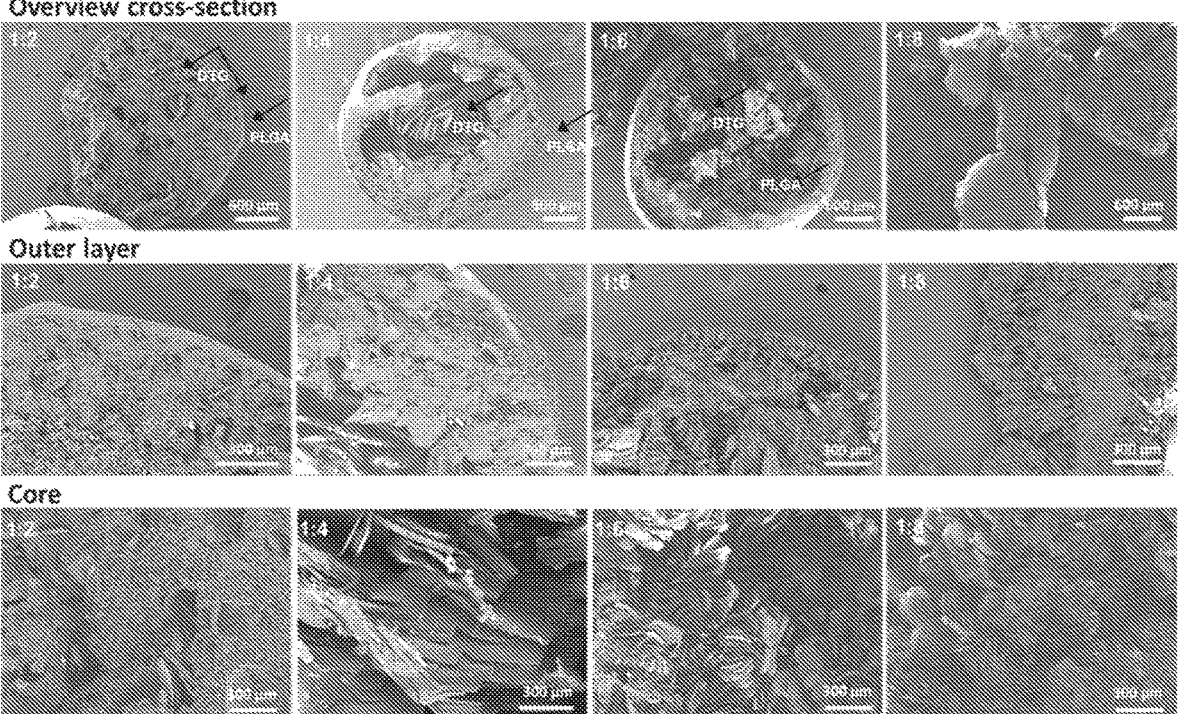
FIG. 4. SEM images representing cross-section images of saturated DTG-loaded PLGA implants (1:2, 1:4, 1:6, and 1:8 w/w PLGA/NMP, PLGA MW 27 kDa) post incubation in 0.01M PBS (pH 7.4 with 2% solutol) at 37° C. for 24 h.

The microstructure of the solid PLGA/DTG implants was assessed by SEM imaging. The SEM results showed the differences in drug distribution and microstructure of solid implants prepared from formulations containing different PLGA:NMP ratios. The 1:2 implants contained the highest amount of PLGA and lowest amount of DTG and showed uniform distribution of DTG within the implants compared to depots made from formulations containing 1:4, 1:6 and 1:8 PLGA/NMP ratios. The distribution of DTG in depots made with 1:4 and 1:6 PLGA/NMP formulations was mostly within the core of the implant with minimum DTG present in the PLGA outer shell of the implant. (FIG. 4).

Effect of PLGA/NMP Weight Ratio on DTG Release Kinetics.

Figure 5:
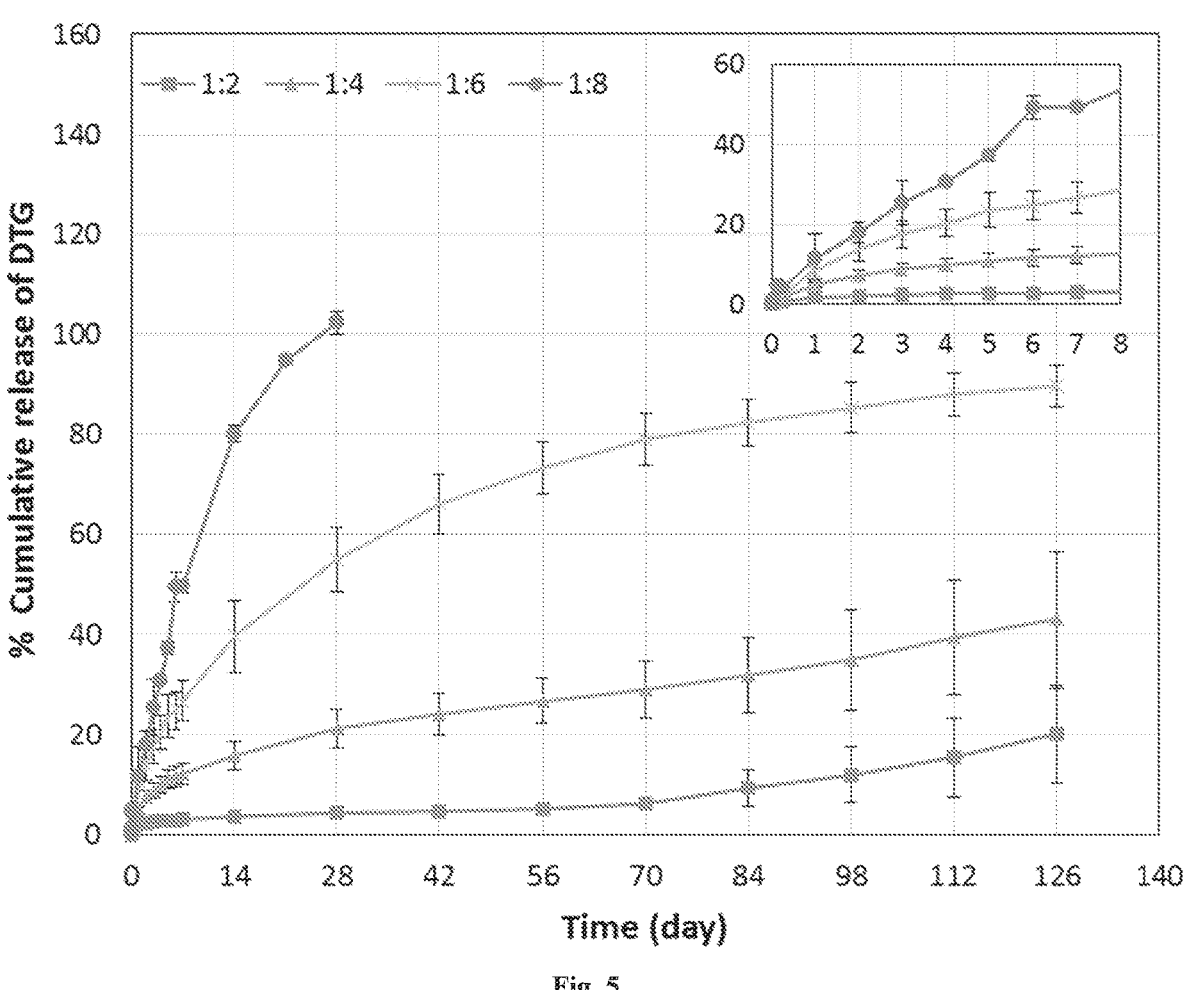
FIG. 5. In vitro release kinetics of DTG from PLGA solid implants fabricated with a range of PLGA:NMP ratios (1:2, 1:4, 1:6, 1:8 w/w). Implants were incubated in 0.01M PBS (pH 7.4 with 2% solutol) at 37° C. for 126 days. Each implant contained maximum concentration of DTG. All error bars represent standard deviation for n=4. The ratio of PLGA:NMP had a direct effect on the release profile of DTG from the implant where higher PLGA/NMP weight ratios resulted in faster DTG release rates.

To investigate the effect of PLGA:NMP ratios on DTG release kinetics, ISFI formulations were prepared with varying PLGA/NMP ratios (1:2, 1:4, 1:6, 1:8) and loaded with maximum drug concentration. Evident from FIG. 5, slower release rate was observed for formulations containing higher PLGA ratios. Greater weight ratios of PLGA in the formulation resulted in more dense depots leading to slower drug diffusion and slower release of DTG (~5% at week 4 for 1:2 formulation) compared to the formulation containing the lowest weight ratio of PLGA, which exhibited the fastest release of DTG (100% within 4 weeks for 1:8 w/w PLGA/NMP formulation) (FIG. 5). The average DTG release per day with zero order kinetics was 23, 45, 277, and 1546 ng/mL for the 1:2, 1:4, 1:6, and 1:8 ratio PLGA:NMP formulations respectively (Table 4 below). A target [DTG]

for inhibition of HIV transmission is equal to or more than 4 times its IC90. Hence, this data allows us to select an appropriate PLGA:NMP ratio to achieve a specific target drug release rate with the ability to improve the drug loading capacity of an implant.

TABLE 4

In vitro DTG release per day and its relative ratio to the protein-adjusted 90% inhibitory concentration (IC90) of DTG for wild-type virus at zero order kinetics. Implants were fabricated at varying PLGA:NMP ratios with saturated DTG concentration.

| Formulation | DTG released per day (μg) |
| --- | --- |
| 1:2 | 0.80 ($R^2$ = 0.9910) |
| 1:4 | 12.72 ($R^2$ = 0.9856) |
| 1:6 | 55.34 ($R^2$ = 0.9734) |
| 1:8 | 309.76 ($R^2$ = 0.9506) |

Example 5

The Use of a Co-Solvent to Enhance Drug Loading in PLGA Solid Implants.

The following studies were carried out with formulations containing 1:6 w/w PLGA/NMP, which exhibited optimum DTG release kinetics (i.e. release rate and duration).

Effect of Co-Solvent on Drug Loading Capacity.

Co-solvents were used to assess an increase in solubility of DTG in the 1:6 w/w PLGA:NMP formulation. Eight biocompatible solvents were investigated as co-solvents with NMP (data not included) to assess an increase in solubility compared to NMP only. DMSO and Gelucire® (44/14) showed improved DTG solubility when used as co-solvents at a 9:1 weight ratio with NMP. With DMSO, the solubility of DTG increased from ~232 mg/mL (NMP only) to ~277 mg/mL (NMP/DMSO 9:1 w/w). With Gelucire® (44/14) (Gel), the solubility of DTG increased from ~232 mg/mL to ~260 mg/mL (NMP/Gel).

TABLE 5

Loading capacity of DTG in varying co-solvents in 1:6 PLGA:solvent formulations (n = 4).

| Solvent system | DTG loading capacity | |
| --- | --- | --- |
| | w/w (mg/g) | w/v (mg/mL) |
| 1:6 PLGA:NMP | 210.81 ± 2.90 | 231.89 ± 3.19 |
| 1:6 PLGA:NMP-DMSO[1] | 251.90 ± 8.20 | 276.64 ± 9.02 |
| 1:6 PLGA:NMP-Gelucire44[2] | 235.99 ± 5.57 | 259.59 ± 6.13 |

[1]The ratio of NMP:DMSO in the solution formulation was 9:1 w/w.
[2]Gelucire44 (Gelucire44/14). The ratio of NMP:Gelucire44 was 9:1 w/w.

Effect of Co-Solvent on Drug Entrapment.

Percent drug entrapment was quantified in the 1:6 w/w PLGA/solvent formulations containing NMP only as solvent or NMP/DMSO (9:1 w/w) as a solvent combination. DTG was added at saturation concentration in each formulation. Solid implants were fabricated by injecting 25 μL of formulation solution into 2 mL of 0.01M PBS (pH 7.4) and incubating at 37° C. for 24 h. The percent drug entrapment in the implants was quantified by HPLC. The results shown in Table 6 below demonstrated that the volume of the medium used to form the solid implants by phase inversion (2 mL of PBS) influenced drug entrapment within the depot.

Optimum drug entrapment (96.6%) was achieved with a smaller volume of PBS (2 mL) compared to 92.3% drug entrapment with 15 mL of PBS (Table 3 above). Using DMSO as a co-solvent with NMP and lowering the volume of PBS used for phase inversion to form the depot (from 15 mL to 2 mL) further enhanced DTG entrapment in the solid implants to 98%.

TABLE 6

Percent entrapment of DTG in solid implants fabricated with 1:6 PLGA:NMP (n = 4) or 1:6 PLGA/(NMP:DMSO).

| Implant formulation | Drug entrapment (%) |
| --- | --- |
| 1:6 PLGA:NMP | 96.68 ± 0.40 |
| 1:6 PLGA:NMP-DMSO[1] | 98.19 ± 0.17 |

[1]The used ratio of NMP:DMSO is 9:1 w/w.

Effect of Co-Solvent on DTG Release Kinetics.

Figure 6:
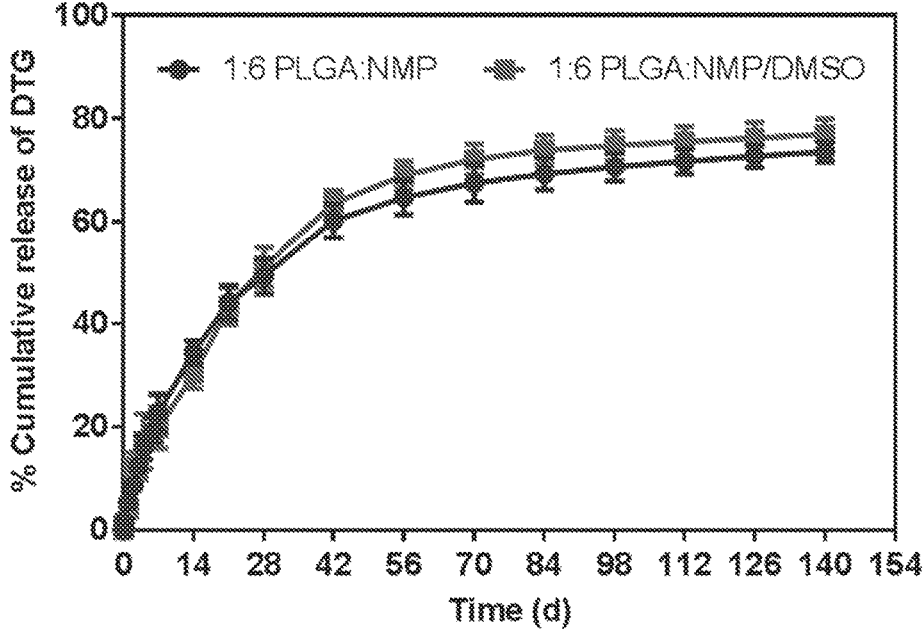
FIG. 6. In vitro release kinetics of DTG from PLGA solid implants fabricated with 1:6 w/w PLGA/NMP or 1:6 w/w PLGA/(NMP:DMSO). Solid implants were incubated in 0.01M PBS (pH 7.4 with 2% solutol) at 37° C. for 140 days. All error bars represent standard deviation for n=4.

In this study, the effect of DMSO as co-solvent in the 1:6 PLGA: solvent formulation on the release kinetics of DTG was investigated. ISFI formulations were prepared with 1:6 PLGA/NMP or 1:6 PLGA/(NMP:DMSO) and loaded with its maximum drug concentration (210 mg/g and 250 mg/g, respectively). Following depot formation via phase inversion, residual solvent and water were removed using a rotary-evaporator for 1 h. As shown in FIG. 6, the use of DMSO as co-solvent in the formulation did not alter the release kinetics of DTG compared to the formulation that did not contain DMSO (i.e. 1:6 PLGA:NMP formulation). The average [DTG] released per day at zero order kinetics within the first 30 days was ~0.47 μg/mL and 0.51 μg/mL for the 1:6 PLGA/NMP and 1:6 PLGA/(NMP:DMSO) formulations respectively (Table 7 below). This data showed that by introducing DMSO as a co-solvent, drug loading capacity in a solid PLGA implant was significantly increased while maintaining the same release kinetics from the implant. This is particularly important as it demonstrates the ability to control drug release kinetics and maximize drug loading concentrations within a solid implant.

TABLE 7

In vitro DTG release per day and its relative ratio to the IC90 of DTG at zero order kinetics within the first 30 days.

| Formulation | DTG released per day (μg) |
| --- | --- |
| 1:6 PLGA:NMP | 103.84 ($R^2$ = 0.9525) |
| 1:6 PLGA:NMP-DMSO | 102.49 ($R^2$ = 0.9599) |

Effect of Co-Solvent on Implant Long-Term Stability.

Figure 7A:
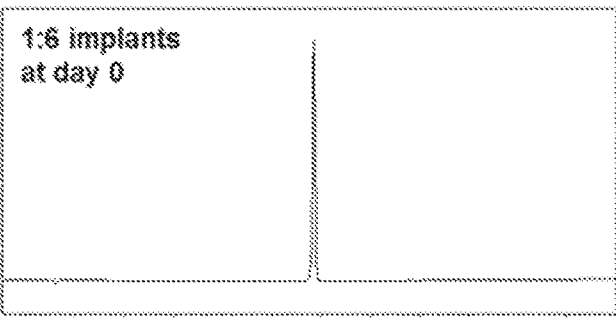
FIGS. 7A-7F. HPLC chromatograms of DTG in dry solid PLGA implants fabricated with 1:6 w/w PLGA/NMP and 1:6 w/w PLGA/(NMP:DMSO) before (FIGS. 7A-7B), and after storage at 40° C. and 75% relative humidity (RH) for 30 days (FIGS. 7C-7D). The physical appearances of the dry solid PLGA implants fabricated by 1:6 PLGA/NMP, and 1:6 PLGA/(NMP:DMSO) before (FIG. 7E) and after storage at 40° C. and 75% RH for 30 days (FIG. 7F).
Figure 7B:
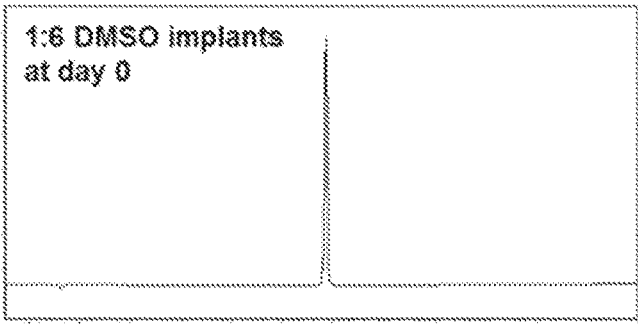
Figure 7C:
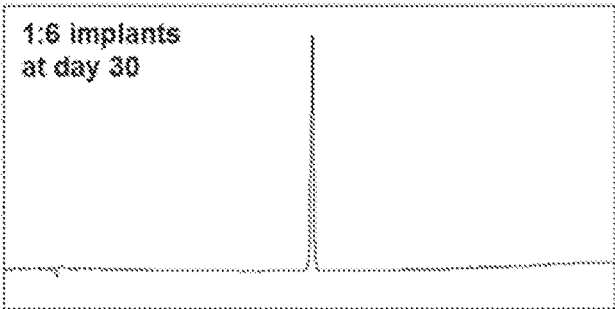
Figure 7D:
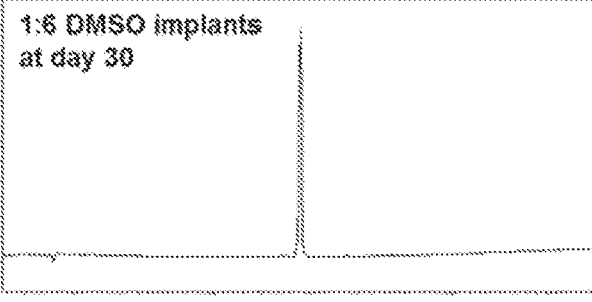
Figure 7E:
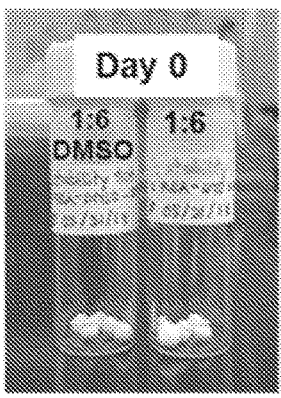
Figure 7F:
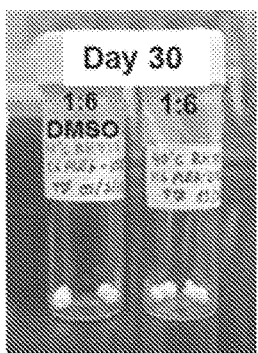

In this study, the stability of solid DTG-loaded implants was investigated. Residual solvent/water was removed from solid depots using a rotary-evaporator for 1 h. Both DTG-loaded implants, 1:6 PLGA/NMP and 1:6 PLGA/(NMP:DMSO) were chemically and physically stable at 40° C. with 75% RH for at least 30 days based on the concentration of DTG quantified by HPLC (Table 8 below), and the physical appearance of the solid implants at various time points (FIGS. 7E and 7F). No degradation products were detected by HPLC analysis (FIGS. 7A-7D).

TABLE 8

DTG concentration in dry solid implants (1:6
PLGA/NMP, and 1:6 PLGA/(NMP:DMSO 9:1) stored
at 40° C. and 75% RH for varying time.

| Storage | DTG concentration (mg/g) | |
|---|---|---|
| time (day) | 1:6 implants | 1:6 DMSO implants |
| 0 | 583.22 ± 3.29 | 600.12 ± 10.59 |
| 7 | 539.45 ± 13.51 | 600.38 ± 13.91 |
| 14 | 586.48 ± 10.72 | 612.02 ± 14.28 |
| 30 | 594.00 ± 8.77 | 632.33 ± 6.57 |

Example 6

Figure 9A:
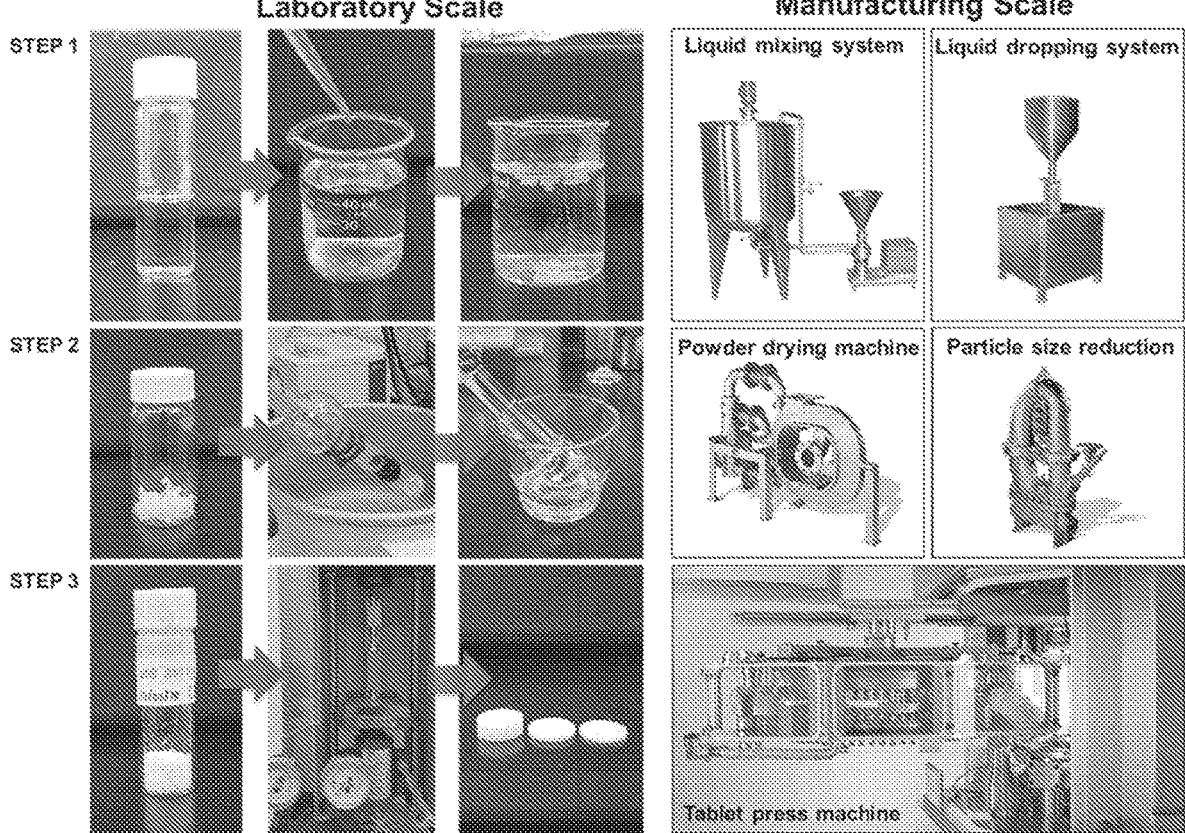
FIGS. 9A-9C.
Figure 9B:
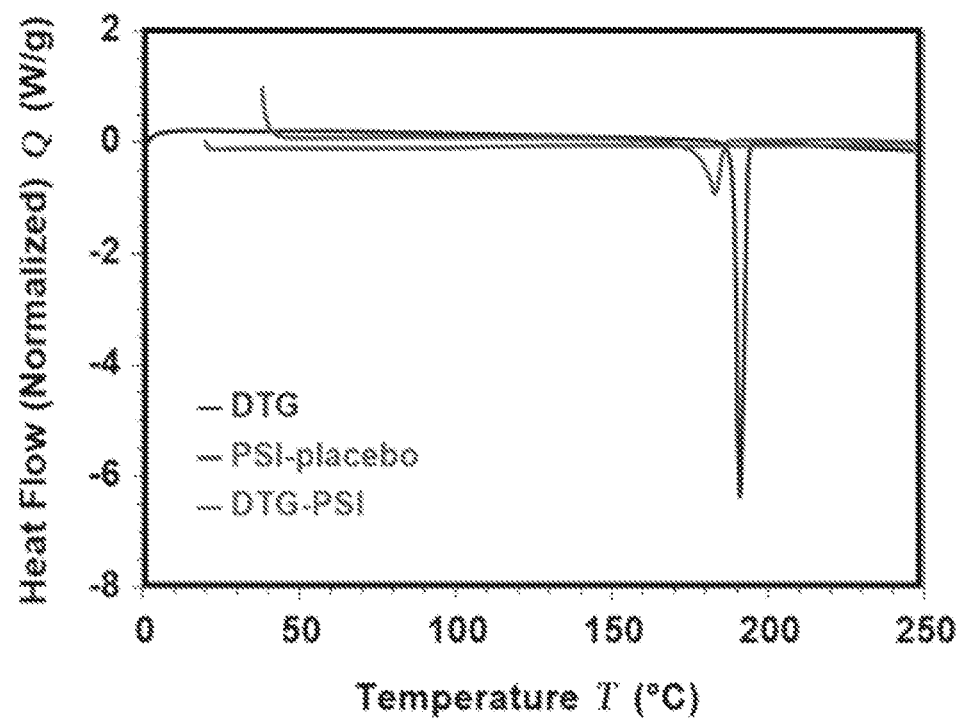
Figure 9C:
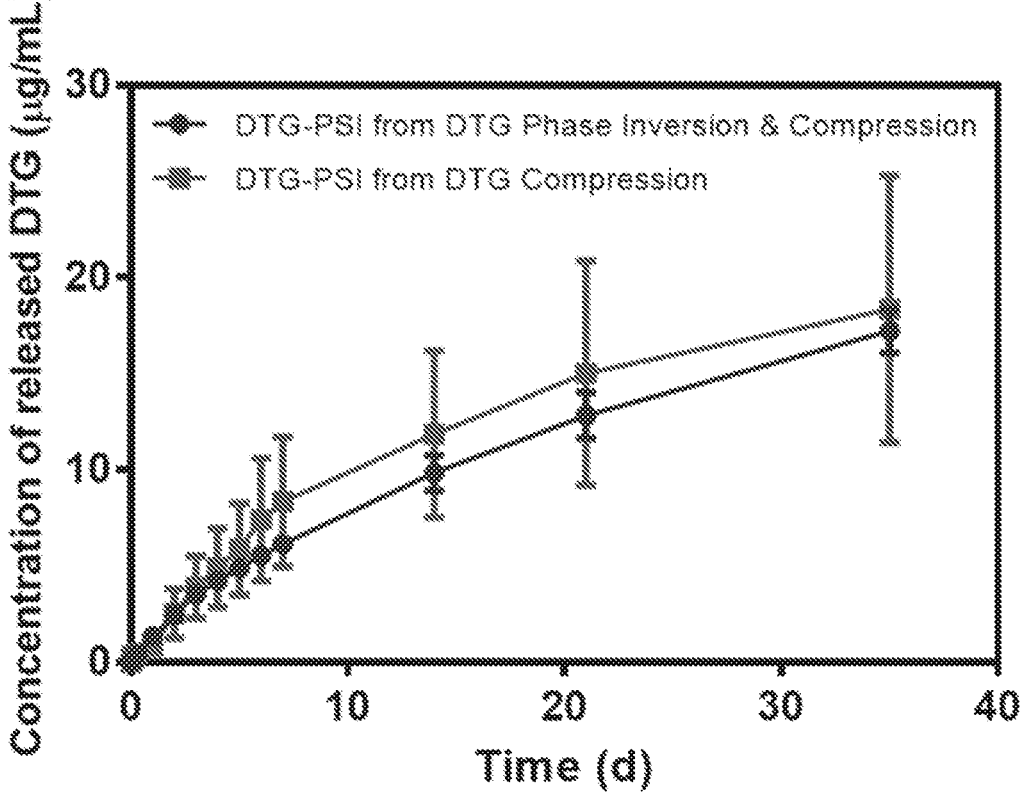
Figure 10A:
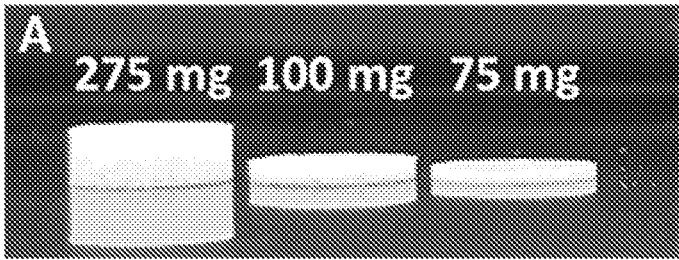
FIGS. 10A-10D. Solid tablets with a range of thickness; a range of drug loading 10-275 mg DTG/tablet (FIGS. 10A and 10B); and a range of sizes (FIGS. 10C and 10D); can be fabricated using direct compression process with different compression tools.
Figure 10B:
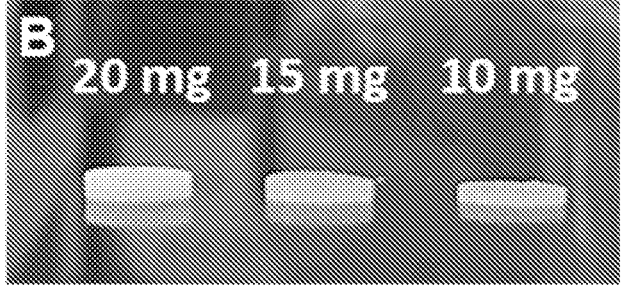
Figure 10C:
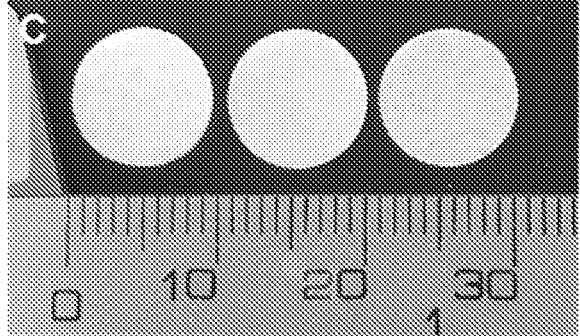
Figure 10D:
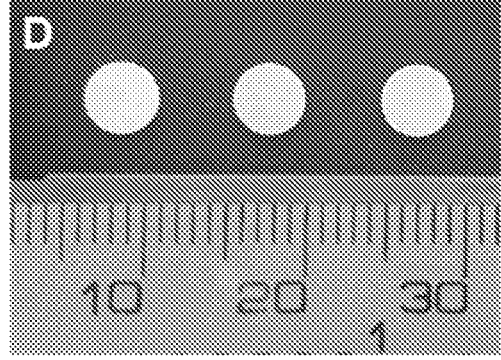
Figure 11:
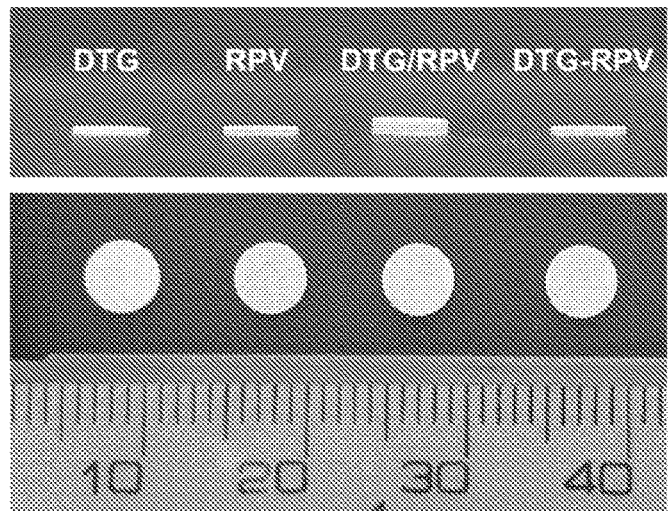
FIG. 11. Various types of drug-loaded solid implants, including from left to right: DTG-only, RPV-only, sandwich DTG/RPV, and co-formulated-DTG/RPV loaded PLGA tablets, fabricated using a combination of phase inversion of DTG-loaded 1:6 PLGA/(NMP:DMSO) and direct compression process (compression force at 0.25 US.ton per 4.8 mm-diameter tablet).

Fabrication of Solvent-Depleted PLGA Solid Tablets by Phase Inversion and Direct Compression Techniques To achieve a target human dose of DTG (600 mg), about 1 g of the dry PLGA implant should be fabricated with the 1:6 PLGA/(NMP:DMSO) formulation. In this report, a direct compression technique was successfully used to produce solid tablets containing high DTG concentrations within a compact implant size. Dry PLGA/drug implants were micronized using a mortar and pestle. DTG distributed uniformly within the micronized PLGA powder at a concentration of 775 mg/g by HPLC analysis (Table 9 below). The micronized PLGA/drug powder (~75 mg) was loaded onto the tablet press machine without any extra-excipients/stabilizers, and finally pressed to produce a compact solid tablet (FIG. 8). Unlike other solid implant forming technologies, the phase inversion and direct Compression processes are simple, scalable, and can accommodate high drug concentrations without the use of heat during the process. This holds myriad benefits for a variety of drugs including biologics and heat sensitive molecules. This technology also allows the fabrication of solid implants with a range of sizes (FIG. 9A) and shapes. This is particularly important to optimize drug dose and increase patient compliance. This combination technology is unprecedented and pertains to the innovation of the proposed fabrication process for high drug loaded solid implants.

TABLE 9

DTG concentration in the micronized PLGA/DTG powder (n =
4) from the solid depots fabricated with 1:6 PLGA/(NMP:DMSO 9:1).

| | DTG in the solution formulation | | DTG in the micronized powder | |
|---|---|---|---|---|
| Formulation | w/w (mg/g) | % w/w | w/w (mg/g) | % w/w |
| 1:6 PLGA/(NMP:DMSO) | 231.26 ± 7.26 | 23.10 | 774.87 ± 24.97 | 77.50 |

Example 7

Fabrication of Multi-Drug Solid Tablets by Phase Inversion and Direct Compression Techniques Solid tablets containing two antiretroviral drugs (dolutegravir (DTG) and rilpivirine (RPV)) were prepared by two different techniques. In the first technique, dry micronized powders of PLGA/DTG and PLGA/RPV were prepared and pre-mixed and subsequently compressed to form a single tablet containing PLGA loaded with DTG and RPV. In the second technique, dry micronized powders of each PLGA/DTG and PLGA/RPV were prepared, compressed into two separate tablets, then the two tablets were sandwiched and compressed to form a single tablet (DTG-s-RPV tablet, "s"=sandwiched) (FIGS. 10A-10D and 11).

Figure 12:
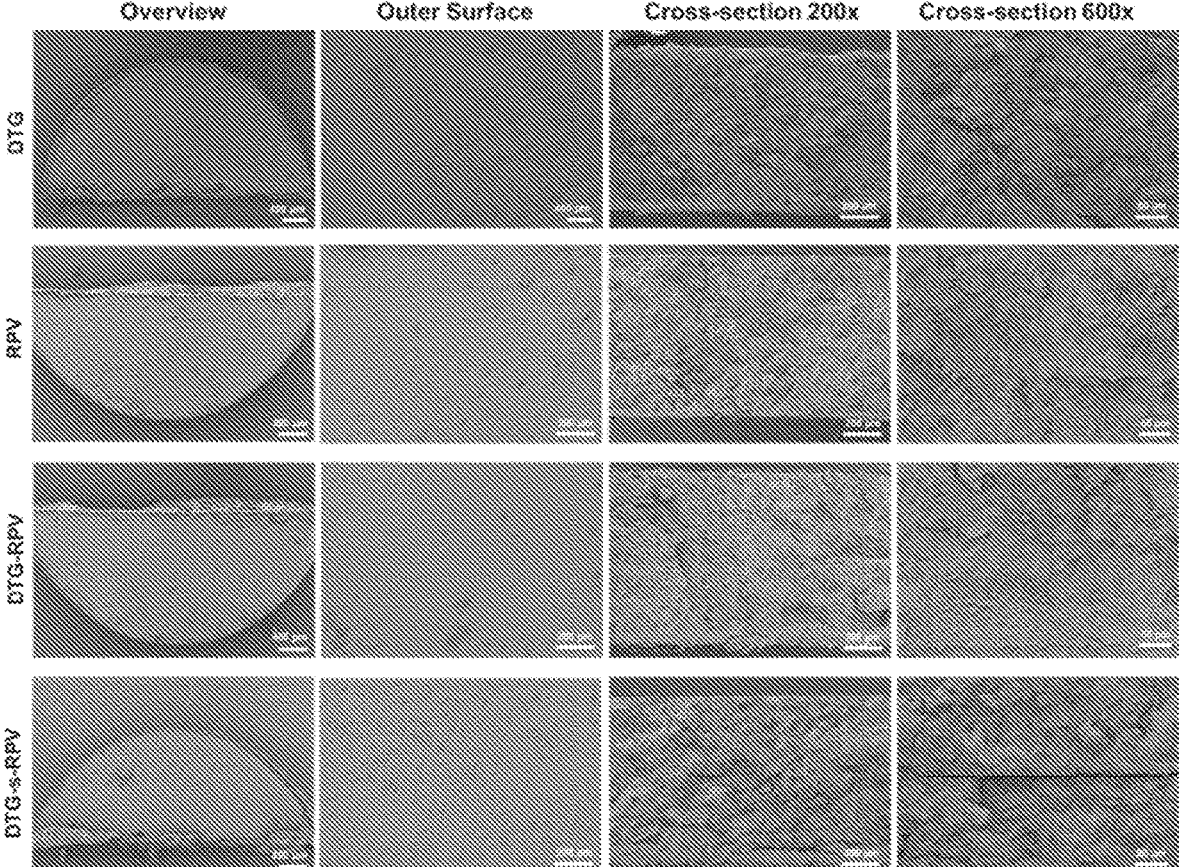
FIG. 12. SEM images representing cross-section images of DTG-loaded, RPV-loaded, co-formulated-DTG/RPV, and sandwich DTG/RPV loaded PLGA tablets fabricated by a combination of phase inversion of drug-loaded 1:6 w/w PLGA/(NMP:DMSO) and direct compression process (compression force at 0.25 US.ton per 4.8 mm-diameter tablet).

The microstructure of the solid single and dual drug tablets was assessed by SEM imaging. The SEM results showed that the drugs were homogenously distributed within the tablet and there was no distinct structural difference between single and dual drug tablets. (FIG. 12). At higher magnification (×600), there is a clear distinction between the sandwiched tablets and the single tablets where the separation between the two tablets can be seen.

Drug Release Kinetics of DTG from the PLGA Solid Tablets.

Figure 13:
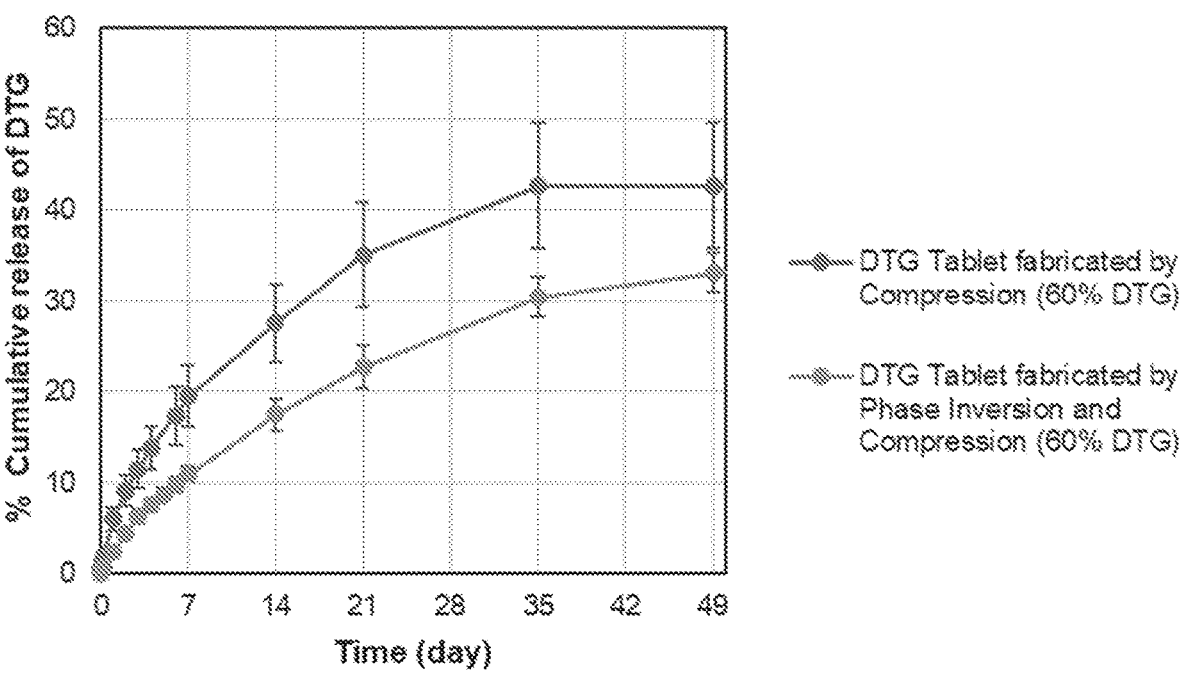
FIG. 13. In vitro release kinetics of DTG from PLGA solid tablets fabricated by 1) a combination of phase inversion of DTG-loaded 1:6 w/w PLGA/(solvent) followed by direct compression process (compression force at 1 US.ton); 2) a direct compression process of a mixture of placebo PLGA dry powder obtained from phase inversion and neat DTG powder (compression force at 1 US.ton). Tablets were incubated at 37° C. in 0.01M PBS (pH 7.4 with 2% solutol) and data collected over 49 days (last timepoint collected, ongoing studies). Error bars represent standard deviation of n=3 samples.

In vitro release of DTG from PLGA solid tablets fabricated by a combination of phase inversion and compression techniques was investigated. The PLGA/(NMP:DMSO) formulation was selected as a prototype formulation and contained a concentration of DTG of 775 mg/g of dry micronized PLGA/drug powder. As shown in FIG. 13, DTG tablets fabricated through a phase inversion of DTG formulated into placebo solutions followed by a direct compression process showed a minimum burst release of DTG within 24 h followed by sustained drug release kinetics over time. In comparison, DTG tablets fabricated by direct compression of DTG powder (as purchased) with PLGA powder obtained from phase inversion of placebo solution showed a higher burst release of DTG and a higher variation in the drug release kinetics. These results demonstrate that PLGA/DTG solid tablets fabricated by a combination of phase inversion of DTG/PLGA/NMP solution and direct compression processes effectively provided steady initial release kinetics of DTG with low burst release (less than 20%).

Drug Release Kinetics of DTG and RPV from the PLGA Solid Tablets.

Figure 14A:
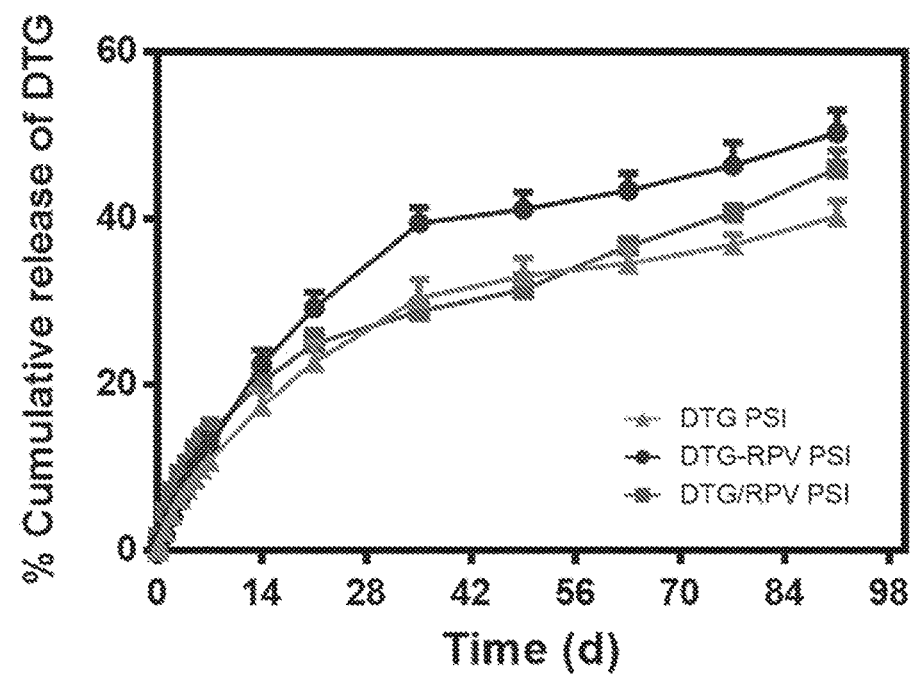
FIGS. 14A-14D. In vitro release kinetics of DTG (FIGS. 14A and 14B) and RPV (FIGS. 14C and 14D) from co-formulated DTG-RPV, and sandwiched DTG/RPV PLGA solid tablets fabricated using a combination of phase inversion of DTG-loaded 1:6 w/w PLGA/(NMP:DMSO) and direct a compression process (compression force at 0.25 US.ton per 4.8 mm-diameter tablet). Tablets were incubated at 37° C. in 0.01M PBS (pH 7.4 with 2% solutol) and data collected over 140 days (last timepoint collected, ongoing studies). Error bars represent standard deviation of n=3 samples.
Figure 14B:
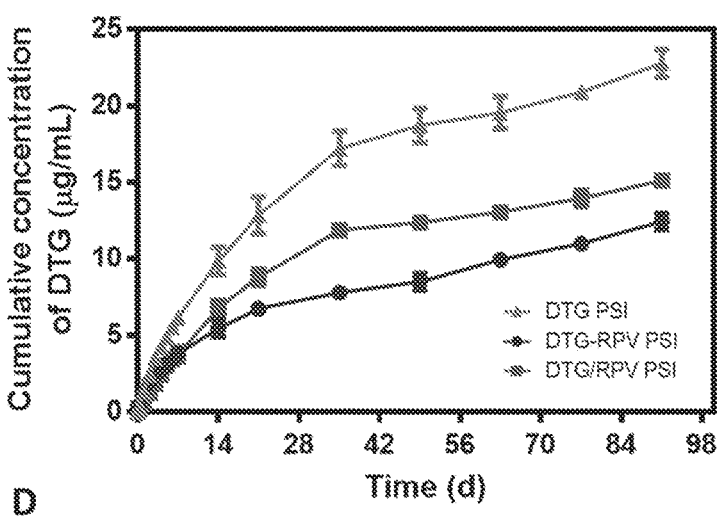
Figure 14C:
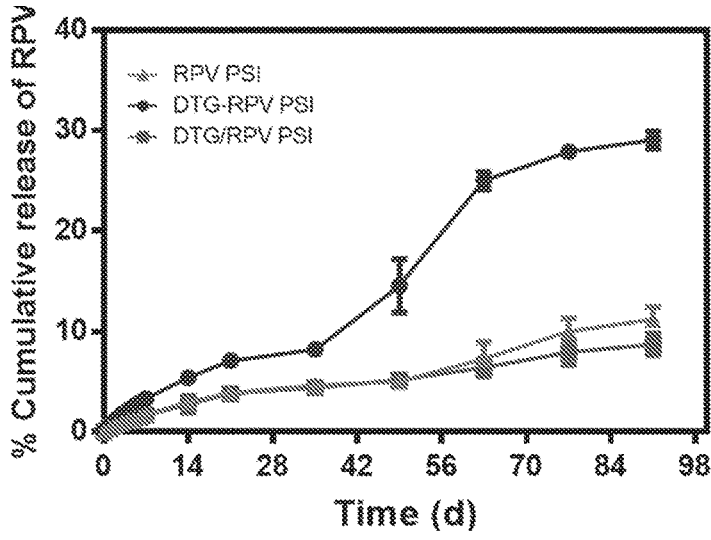
Figure 14D:
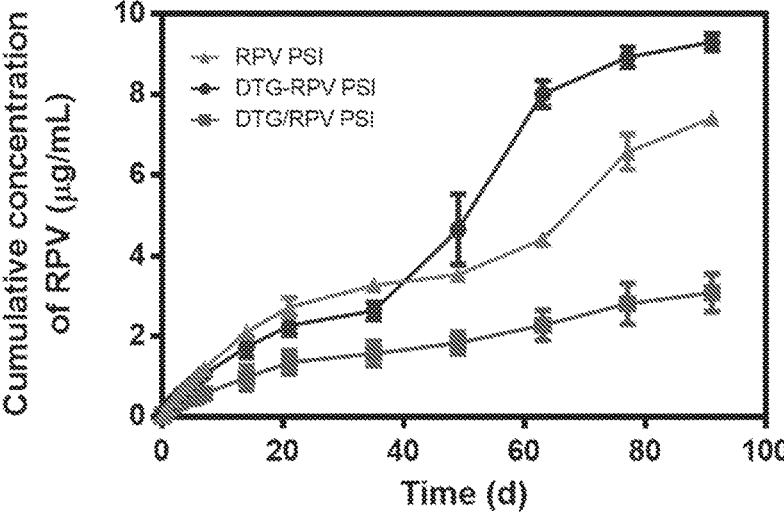

In vitro release of DTG and RPV from PLGA single and dual drug solid tablets fabricated by a combination of phase inversion and compression techniques was investigated. The 1:6 w/w PLGA/(NMP:DMSO) formulation was selected as a prototype formulation and contained a concentration of DTG of 125 mg/g and RPV 125 mg/g of ISFI formulation, resulting in a concentration of DTG at ~300 mg/g and RPV at ~320 mg/g of dry micronized PLGA/drug powder. As shown in FIGS. 14A-14B, when comparing DTG released from dual drug tablets prepared as a single or sandwiched tablet, the release kinetics are very similar. This shows that the tablet preparation (single tablet vs. sandwiched tablets) containing DTG/RPV combination did not affect the release kinetics of DTG. In contrast, the release kinetics of RPV exhibited different profiles when comparing the single tablet to the sandwiched tablet (FIGS. 14C-14D). These data show that the effect of tablet preparation on drug release kinetics is drug specific. See also Tables 10 and 11 below.

TABLE 10

In vitro release kinetics parameters of DTG from different PSI formulations (n = 3)

| Formulation | Wt % of DTG | Total DTG per PSI (mg)* | Burst at 24h (%) | Burst at 24h (µg) | DTG release at zero order** (%/day) | DTG release at zero order** (µg/day) | Zero Order Equation (µg/day) | $R^2$ |
|---|---|---|---|---|---|---|---|---|
| DTG PSI | 58.60 ± 13.05 | 11.23 ± 0.12 | 2.42 ± 0.39 | 1.37 ± 0.21 | 5.66 | 3.16 | y = 0.26x + 2.9 | 0.89 |
| DTG-RPV PSI | 27.76 ± 17.78 | 5.40 ± 0.04 | 1.94 ± 0.53 | 1.26 ± 0.17 | 6.49 | 1.93 | y = 0.13x + 1.8 | 0.90 |
| DTG/RPV PSI | 29.30 ± 6.53 | 6.02 ± 0.18 | 4.67 ± 0.60 | 0.57 ± 0.14 | 7.28 | 1.98 | y = 0.18x + 1.8 | 0.88 |

TABLE 11

In vitro release kinetics parameters of RPV from different PSI formulations (n = 3)

| Formulation | Wt % of RPV | Total RPV per PSI (mg)* | Burst at 24h (%) | Burst at 24h (µg) | RPV release at zero order** (%/day) | RPV release at zero order** (µg/day) | Zero Order Equation (µg/day) | $R^2$ |
|---|---|---|---|---|---|---|---|---|
| RPV PSI | 68.80 ± 17.72 | 13.74 ± 0.28 | 0.30 ± 0.01 | 0.21 ± 0.01 | 0.59 | 0.44 | y = 0.076x + 0.36 | 0.97 |
| DTG-RPV PSI | 32.93 ± 19.38 | 6.40 ± 0.05 | 0.66 ± 0.09 | 0.21 ± 0.03 | 0.67 | 0.22 | y = 0.110x + 0.11 | 0.98 |
| DTG/RPV PSI | 34.40 ± 8.86 | 6.88 ± 0.21 | 0.48 ± 0.01 | 0.17 ± 0.01 | 0.75 | 0.26 | y = 0.033x + 0.23 | 0.97 |

Mechanical Properties of Prototype PLGA Solid Tablets Fabricated at Varying Compression Forces.

Figure 15A:
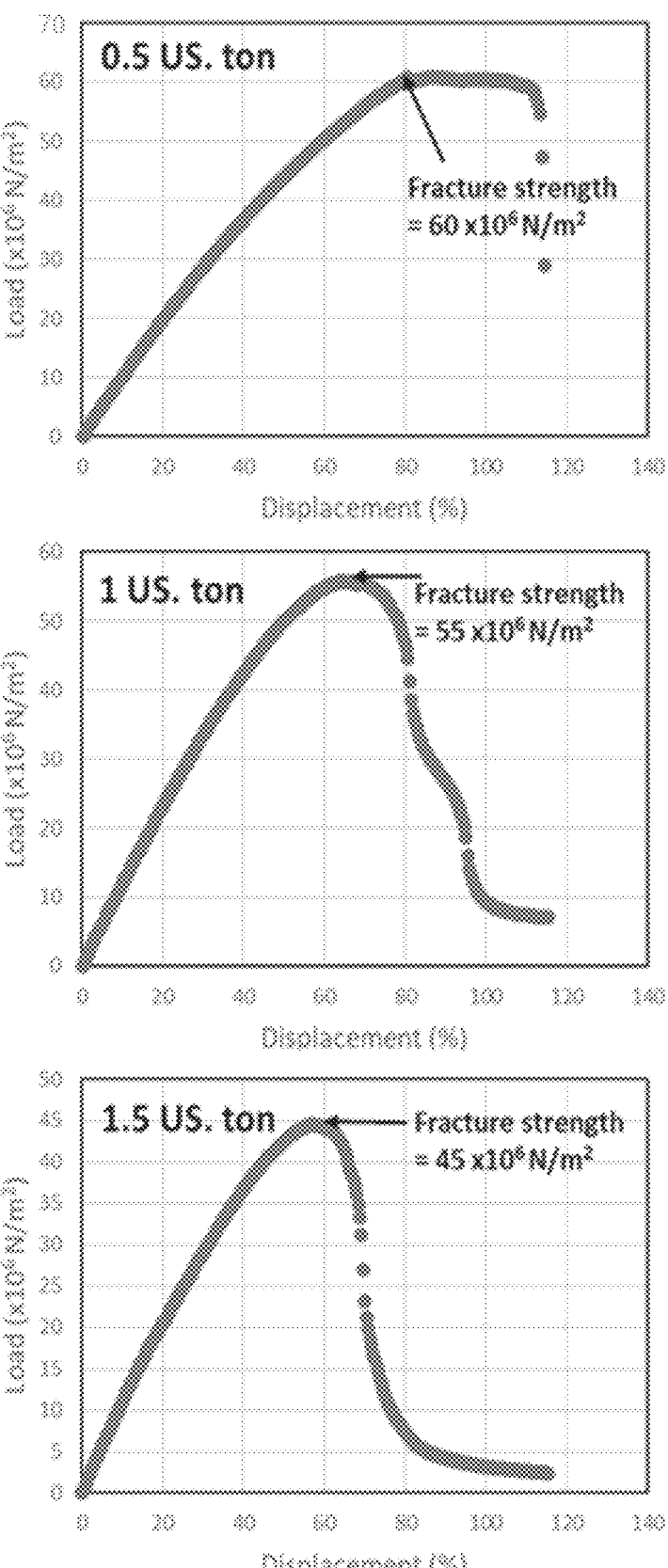
FIGS. 15A-15B. Mechanical properties of prototype solid tablets.
Figure 15B:
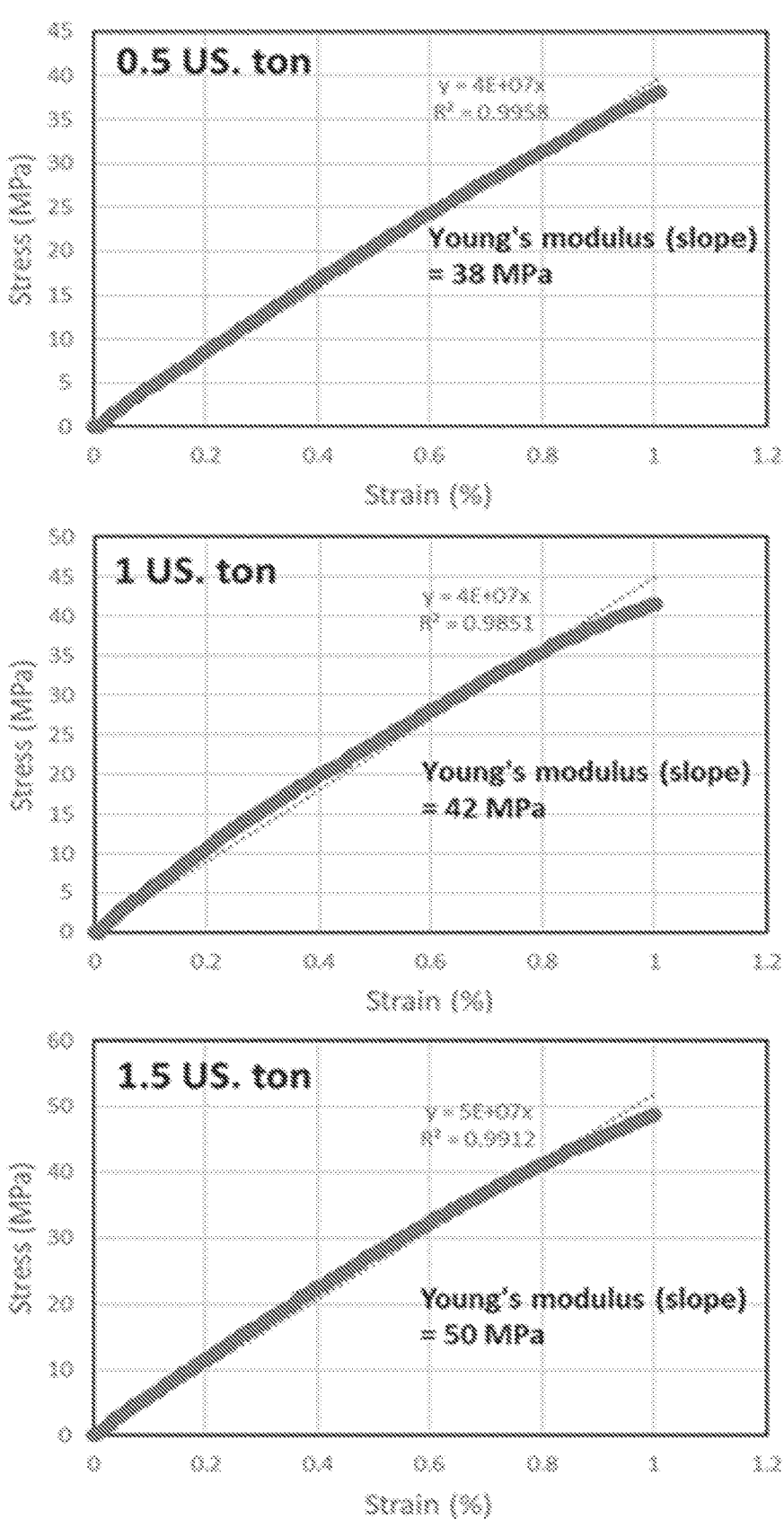

Mechanical properties of solid tablets are essential for handling, transportation, shipping, or breakage during storage and implant usage. Three types of solid tablets were prepared by varying compression force (Table 12 below), and their mechanical properties including, Young's modulus and fracture strength were investigated. Young's modulus measures the resistance of a tablet to elastic deformation under a specific load. A stiff material has a high Young's modulus and changes its shape only slightly under elastic loads. Fracture strength measures the maximum load (stress) that a tablet can handle. Based on the results illustrated in FIG. 15A, tablets fabricated with 0.5 US.ton compression force exhibited the highest fracture strength (60 $MN/m^2$), followed by 1 US.ton tablet (55 $MN/m^2$), and 1.5 US.ton tablet (45 $MN/m^2$). The fracture strength of drug tablets is generally in range of 1 to 2 $MN/m^2$. Based on the results illustrated in FIG. 15B, tablets fabricated with 1.5 US.ton compression force resulted in tablets with the highest stiffness (50 MPa), followed by 1 US.ton tablet (42 MPa), and 0.5 US.ton tablet (38 MPa). Therefore, these results demonstrate that the PLGA solid tablets will maintain their integrity well in vivo. By varying tablet compression forces, this can potentially allow us to further optimize drug release kinetics to achieve target release rates.

Release Kinetics of Prototype PLGA Solid Tablets Fabricated at Varying Compression Forces.

Figure 16:
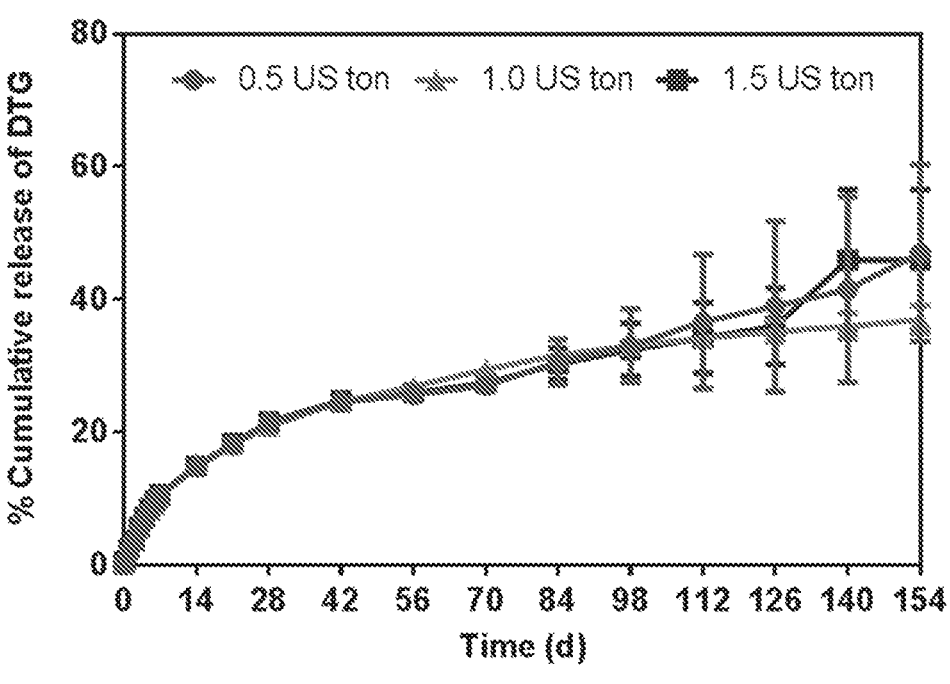
FIG. 16. In vitro release kinetics of DTG from PLGA solid tablets fabricated using a combination of phase inversion (of DTG-loaded 1:6 w/w PLGA/(NMP:DMSO)) and direct compression process at different compression forces (0.5, 1, 1.5 US.ton). Tablets were incubated at 37° C. in 0.01M PBS (pH 7.4 with 2% solutol) and data collected over 154 days (last timepoint collected, ongoing studies). Error bars represent standard deviation of n=3 samples.

In vitro release of DTG from PLGA solid tablets prepared by different compression forces was investigated. The PLGA/(NMP:DMSO) formulation was selected as a prototype formulation and contained a concentration of DTG at 650 mg/g of dry micronized PLGA/drug powder. As shown in FIG. 16, the compressed force of compression process has no impact on the release kinetics of DTG. These results demonstrate that the mechanical properties of PLGA/DTG solid tablets can be easily optimized while maintaining the same release kinetics of targeted drugs.

TABLE 12

Formulation parameters of solid tablets prepared by varying compression forces.

| Formulation | DTG-PLGA powder weight (mg) | Tablet diameter (mm) | Compression force (US. ton) |
|---|---|---|---|
| 1:6 PLGA:NMP-DMSO | 75 | 10 | 1.5 |
| 1:6 PLGA:NMP-DMSO | 75 | 10 | 1.0 |
| 1:6 PLGA:NMP-DMSO | 75 | 10 | 0.5 |

Release Kinetics of Prototype PLGA Solid Tablets Fabricated with a Range of PLGA Molecular Weights.

Figure 17:
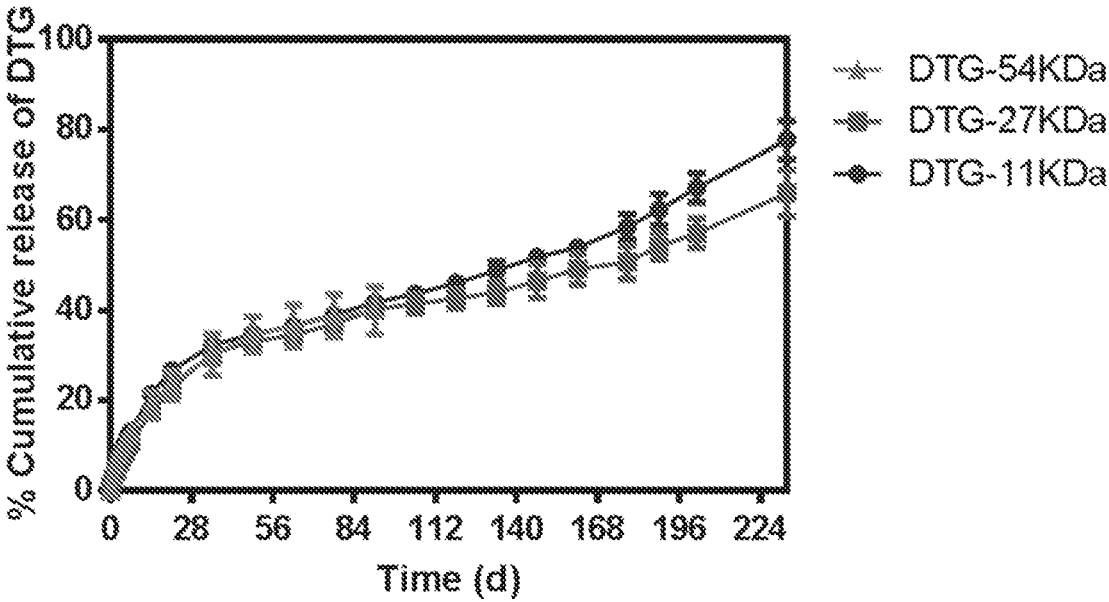
FIG. 17. In vitro release kinetics of DTG from the PSIs fabricated using PLGA with a range of molecular weights and constant DTG loading (at ~570 mg/g). Error bars represent standard deviation of n=3 samples.

Molecular weight (MW) of PLGA is known as a parameter that affects drug release kinetics in drug delivery systems. In general, lower molecular weight polymers result in a higher initial burst and faster release rate due to faster degradation of the polymer backbone via ester hydrolysis. Herein, there was no significant of PLGA MW (11, 27 and 54 kDa) on DTG release kinetics formulated in the various PSIs (DTG 570 mg/g) (FIG. 17). This could be due to the densely packed PLGA-DTG tablet combined with the hydrophobic nature of DTG loaded at very high weight ratio to PLGA (~57 wt. %) limiting the access of aqueous environment to the PLGA network and resulting thus in slow ester hydrolysis for all formulations. The effect of PLGA MW became more visible after 13 weeks, where higher PLGA MW showed slower DTG release kinetics compared to PSIs made with lower PLGA MW (FIG. 17). These results demonstrate that at high packing density and high weight ratio of a hydrophobic drug, PLGA MW did not exhibit a significant effect on drug release kinetics. The effect of PLGA MW could, however, be more significant at lower drug weight ratios and/or with drugs that have different physical/chemical properties than DTG (i.e. Log P, pKa, MW etc.).

In Vitro Release of DTG Loaded at a Range of Concentrations in Solid Tablets.

Figure 18:
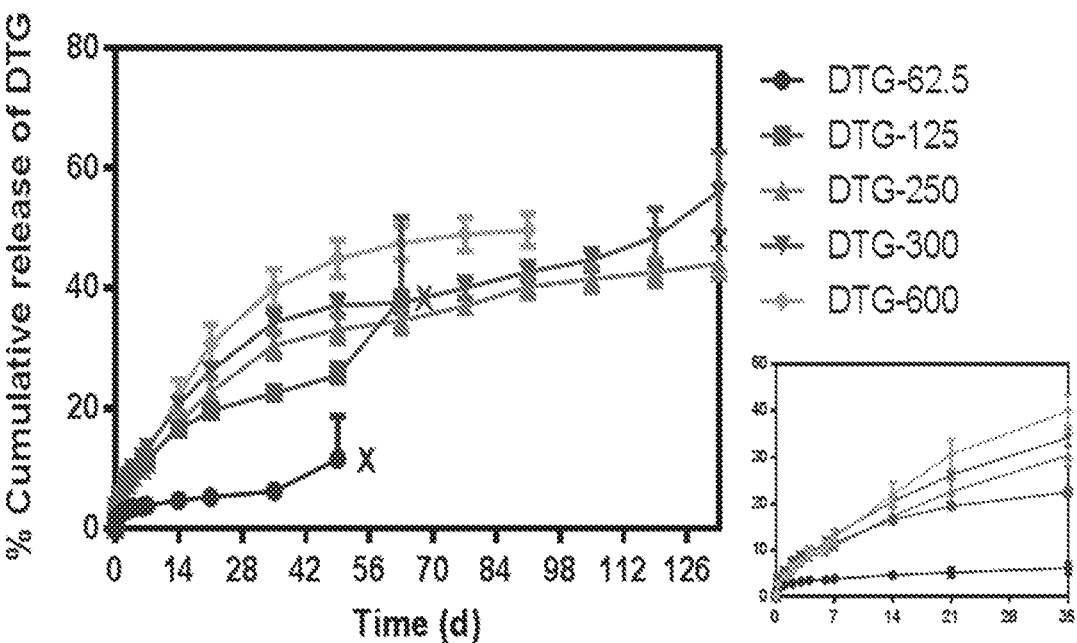
FIG. 18. In vitro release kinetics of DTG from PSIs fabricated with a range of DTG loading in the same formulation (1:6 w/w PLGA:(NMP/DMSO)). DTG loading concentration in the solid tablets quantified by HPLC analysis was 820, 640, 580, 470, 220 mg/g for the following formulations respectively: DTG-600, DTG-300, DTG-250, DTG-125, and DTG-62.5. Error bars represent standard deviation of n=3 samples. x in the graph represents the end of the study which was stopped due to disintegration of the PSI in the release medium.

To investigate the effect of drug loading on release kinetics, DTG PSIs were fabricated with a range of DTG concentrations, including 220, 470, 580, 640, and 820 mg/g tablets. The solution formulations used to fabricate the aforementioned tablets contained 62.5, 125, 250, 300, and 600 mg/g of DTG formulated in a 1:6 PLGA/(NMP:DMSO) respectively (i.e. DTG-62.5, DTG-125, DTG-250, DTG-300, and DTG-600, respectively). The initial release (burst within the first 24 h) as well as the release rate generally increased with increasing drug loading. This is mainly attributed to the fact that at higher drug loading, more drug is distributed throughout the entire implant volume and close to the surface of the solid implant and diffuses out with a greater gradient leading to faster release kinetics (FIG. 18). By varying drug loading, drug release kinetics can be further optimized to achieve different target release rates and durations that can be adapted and controlled for different drugs.

In Vitro Long-Termed Stability of DTG-Loaded PSIs.

Figure 19A:
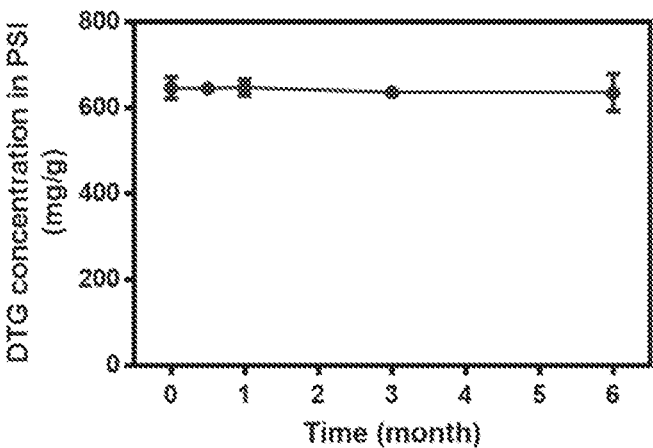
FIGS. 19A-19C. Accelerated stability test of DTG-loaded PSI implants.
Figure 19B:
Figure 19C:
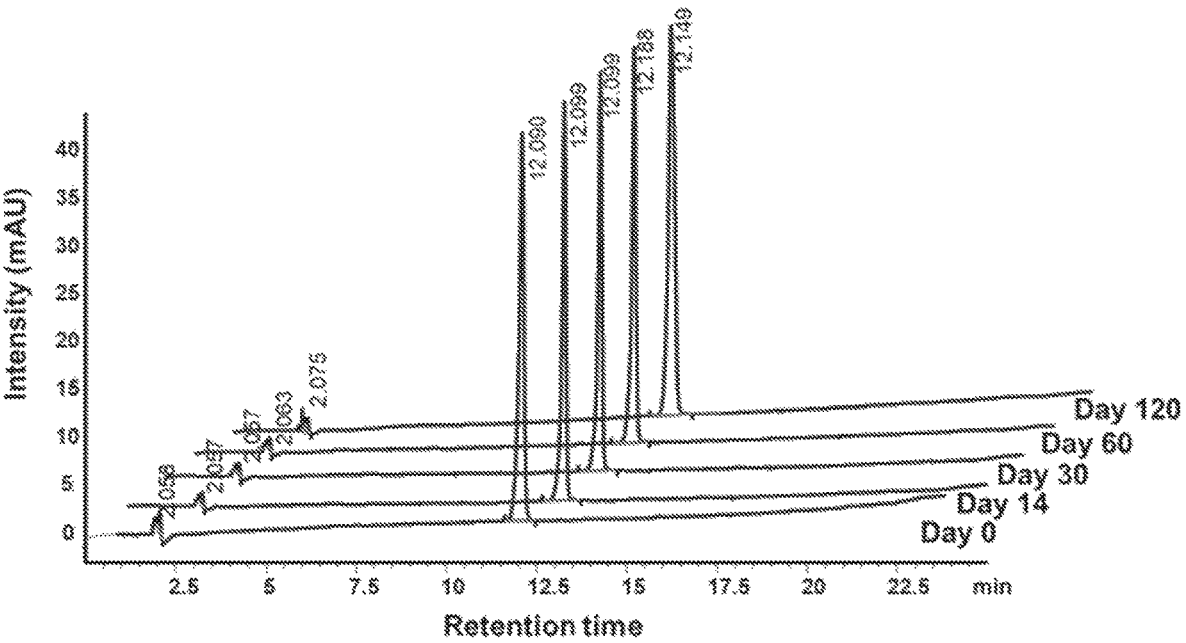

The stability of DTG loaded PSIs was determined using accelerated stability test (storage at 40° C. with 75% RH for 6 months). The DTG-loaded PSIs were chemically stable for at least 6 months based on the concentration of DTG quantified by HPLC (FIG. 19A), and the physical appearance of the solid implants at various time points (FIG. 19B). No degradation products were detected by HPLC analysis (FIG. 19C).

X-Ray Powder Diffraction (XRD) Analysis.

Figure 20A:
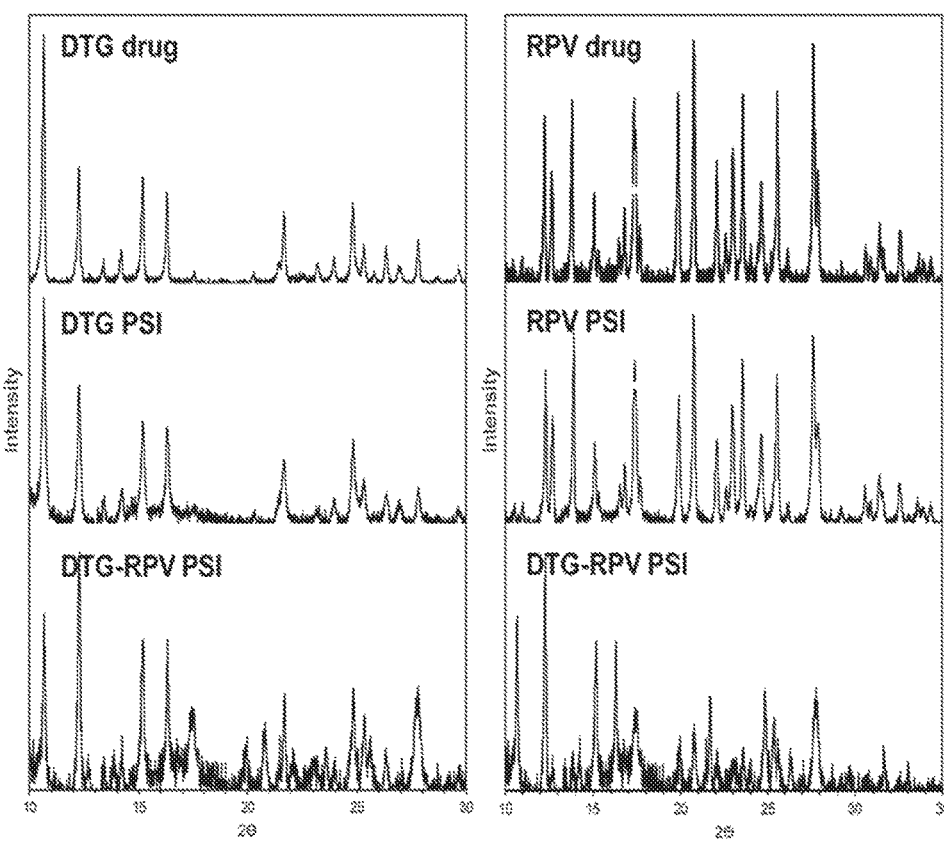
FIGS. 20A and 20B.

XRD analysis was used to assess the impact of preloading of co-drugs in PSI formulations (Table 13) on drug crystallinity patterns. The crystallinity pattern of DTG did not change in either single- or co-formulated PSIs, and exhibited the same relative ratios (peak intensity) compared to neat DTG (FIG. 20A). Similarly, the crystallinity pattern and the relative ratios of RPV were similar in the single RPV-PSIs compared to RPV neat. However, the relative ratios and patterns of RPV changed in the co-formulated DTG-RPV PSI.

TABLE 13

Formulation details of prototype drug-loaded PSIs.

| Implant tablet | Formulation | Total drug loaded (% wt. tablet) | Tablet weight (mg) | Compression force (US. ton) | Diameter (mm) |
|---|---|---|---|---|---|
| DTG | 1:6 PLGA/NMP:DMSO 9:1 | 60 | 20 | 0.25 | 4.76 |
| RPV | 1:6 PLGA/NMP:DMSO 9:1 | 60 | 20 | 0.25 | 4.76 |
| DTG-RPV | 1:6 PLGA/NMP:DMSO 9:1 | 30:30 (DTG:RPV) | 20 | 0.25 | 4.76 |
| DTG/RPV | 1:6 PLGA/NMP:DMSO 9:1 | 30:30 (DTG:RPV) | 20 (10 mg/layer) | 0.25 | 4.76 |

DSC Analysis.

Figure 20B:
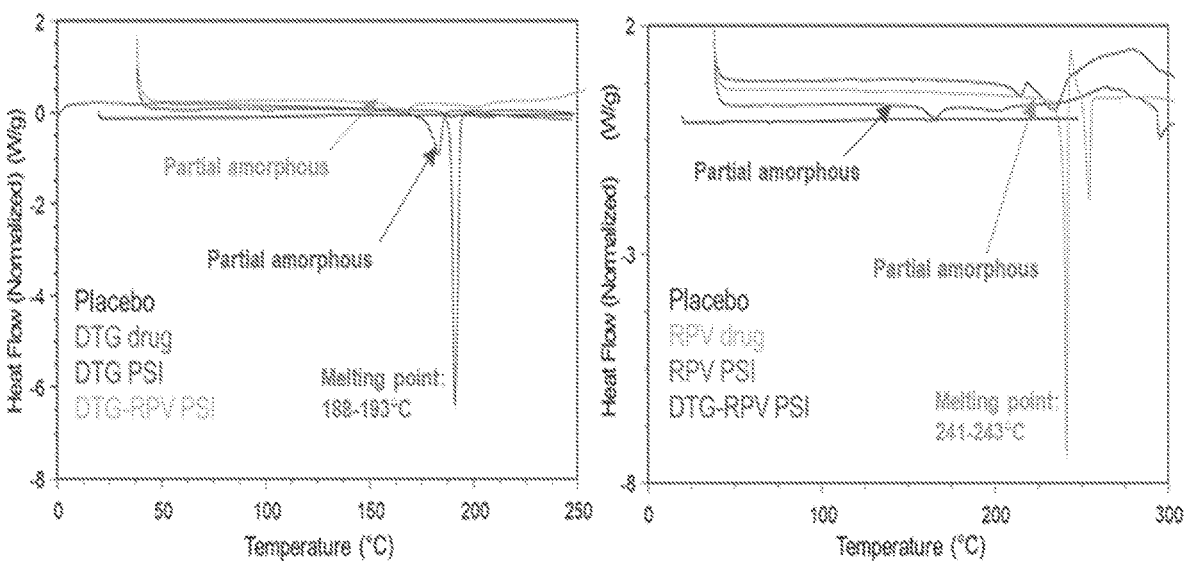

DSC thermograms of neat DTG and RPV compared to DTG-RPV PSI demonstrated a change in drug crystallinity (i.e. from crystalline to amorphous) for both DTG and RPV when formulated in the PSIs (FIG. 20B). Neat DTG and RPV thermograms showed an endothermic peak at 188° C. and 241° C., respectively. The DTG PSI showed a shifted low intensity peak at 168° C., showing that DTG crystallinity was significantly reduced when formulated in the PLGA PSI. Similar to DTG, the thermogram of RPV PSI showed a shifted low intensity peak at 235° C., corresponding to a decrease in RPV crystallinity when formulated in a PSI.

In Vivo Pharmacokinetics.

Figure 21A:
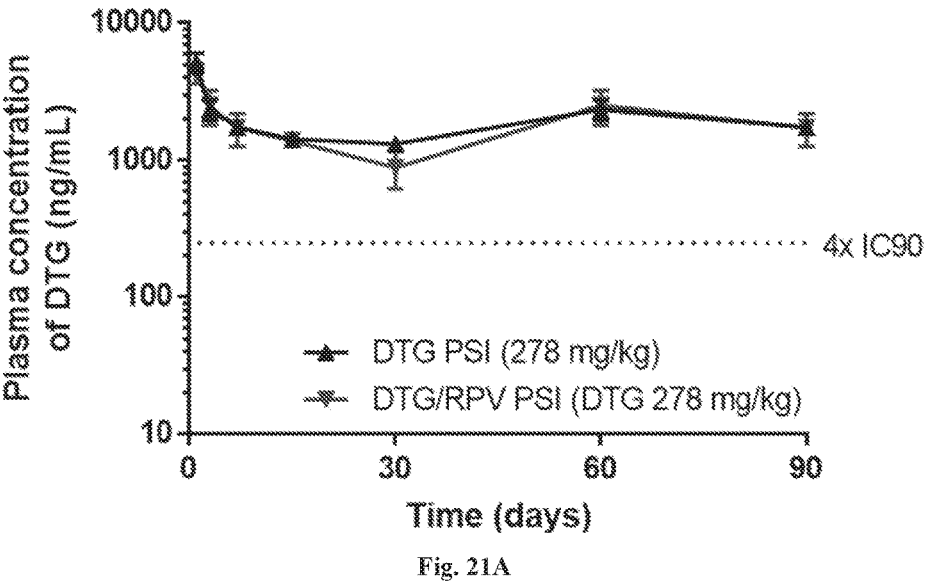
FIGS. 21A-21D.
Figure 21B:
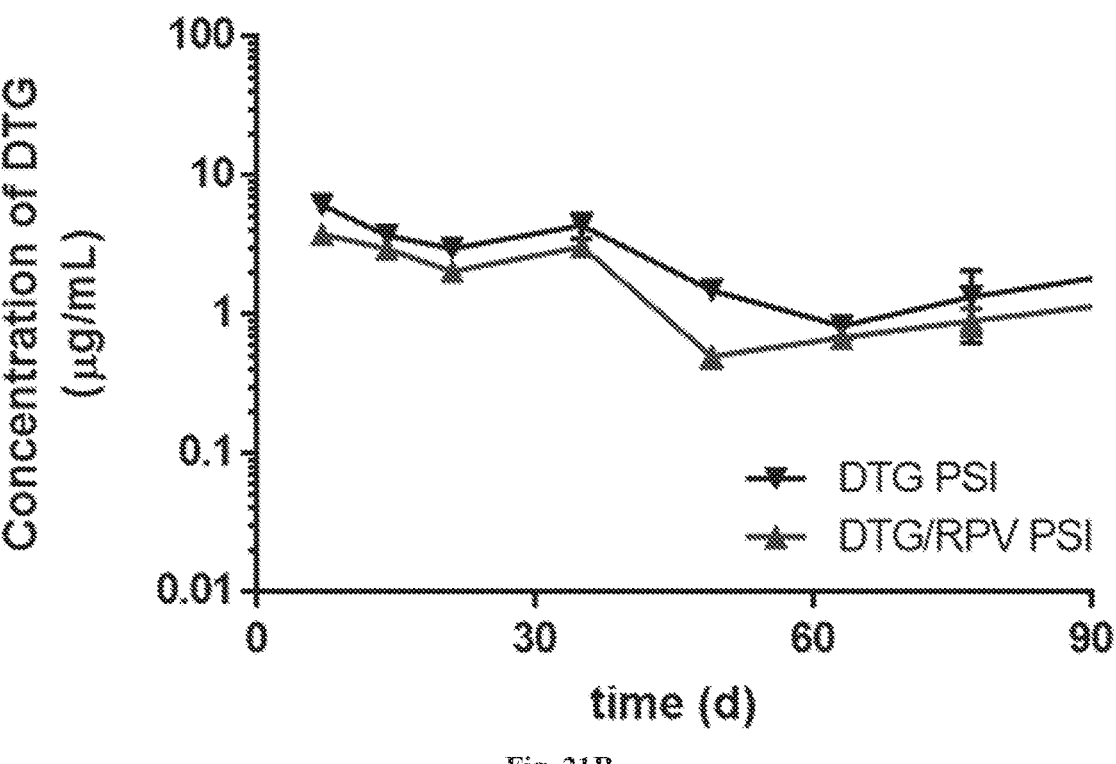
Figure 21C:
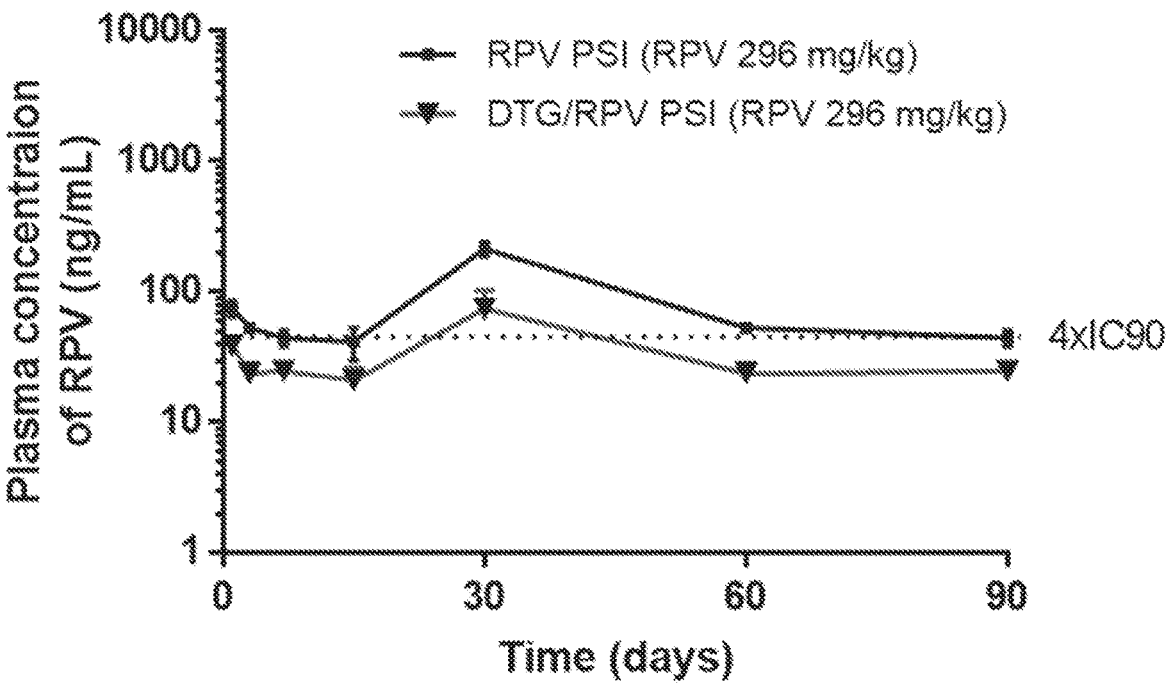
Figure 21D:
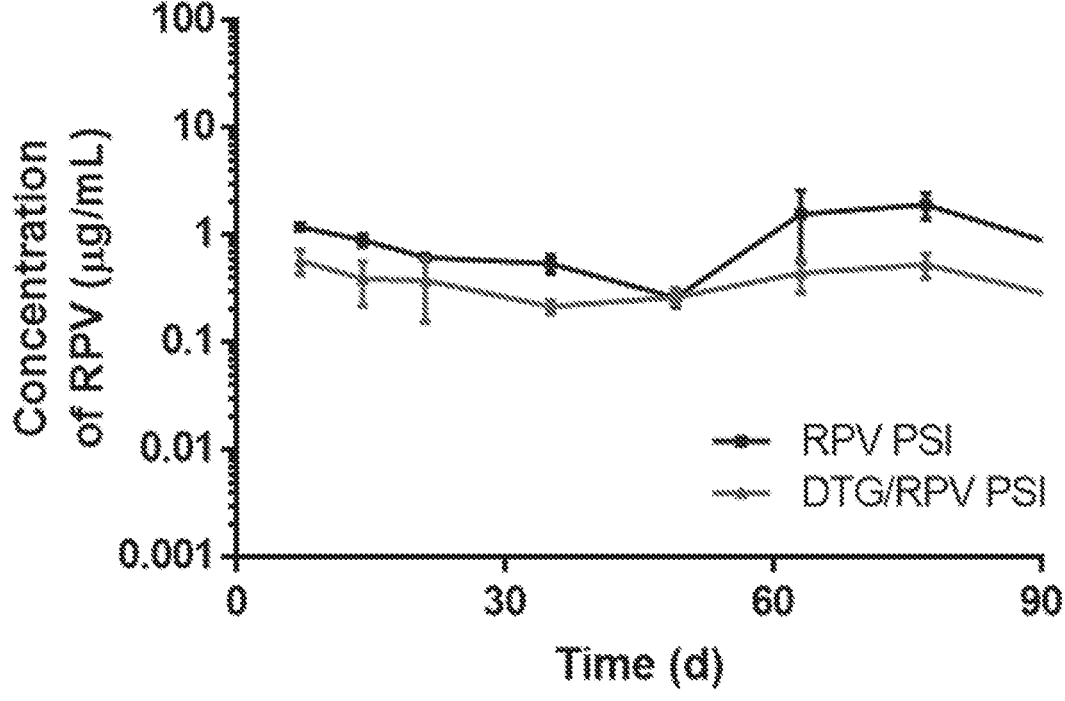

Plasma concentrations of DTG and RPV were quantitated using a validated high-performance liquid chromatography-tandem mass spectrometry LC/MS-MS method. Non-compartmental analysis of the median composite pharmacokinetic (PK) profile of DTG demonstrated a biexponential decay. After an initial 1st order declined in plasma concentration, the release of DTG approached zero-order kinetics. Plasma concentration of DTG was ten times greater than the protein adjusted (PA)-$IC_{90}$ for at least 3 months post administration. In addition, results showed that plasma concentration of DTG was similar when formulated alone (DTG PSI) or in combination with RPV (DTG/RPV PSI; FIGS. 21A and 21 B). Plasma concentrations of RPV when formulated alone (RPV PSI) were at or slightly above 4×IC90 of RPV and slightly below 4×IC90 levels when co-formulated with DTG (DTG/RPV PSI; FIGS. 21C and 21D).

REFERENCES

All references listed herein including but not limited to all patents, patent applications and publications thereof, scientific journal articles, and database entries are incorporated herein by reference in their entireties to the extent that they supplement, explain, provide a background for, or teach methodology, techniques, and/or compositions employed herein.

It will be understood that various details of the presently disclosed subject matter may be changed without departing from the scope of the presently disclosed subject matter. Furthermore, the foregoing description is for the purpose of illustration only, and not for the purpose of limitation.

1. B. Research. April 2014. Diagnostics and Therapeutics for HIV: Global Markets.www.bccresearch.com.
2. WHO—10 Facts on HIV/AIDS, http://www.who.int/features/factfiles/hiv/en/.
3. J. M. Marrazzo, G. Ramjee, B. A. Richardson, K. Gomez, N. Mgodi, G. Nair, T. Palanee, C. Nakabiito, A. Van Der Straten and L. Noguchi. 2015. Tenofovir-based preexposure prophylaxis for HIV infection among African women. N. Engl. J. Med. 372: 509-518.
4. R. M. Grant, J. R. Lama, P. L. Anderson, V. McMahan, A. Y. Liu, L. Vargas, P. Goicochea, M. Casapia, J. V. Guanira-Carranza and M. E. Ramirez-Cardich. 2010. Preexposure chemoprophylaxis for HIV prevention in men who have sex with men. N. Engl. J. Med. 363: 2587-2599.
5. M. Gunawardana, M. Remedios-Chan, C. S. Miller, R. Fanter, F. Yang, M. A. Marzinke, C. W. Hendrix, M. Beliveau, J. A. Moss, T. J. Smith and M. M. Baum. 2015. Pharmacokinetics of Long-Acting Tenofovir Alafenamide (GS-7340) Subdermal Implant for HIV Prophylaxis. Antimicrob. Agents Chemother. 59: 3913-3919.
6. M. Barnhart. 2017. Long-Acting HIV Treatment and Prevention: Closer to the Threshold.Global Health: Science and Practice. 5: 182-187.
7. E. Schlesinger, D. Johengen, E. Luecke, G. Rothrock, I. McGowan, A. van der Straten and T. Desai. 2016. A Tunable, Biodegradable, Thin-Film Polymer Device as a Long-Acting Implant Delivering Tenofovir Alafenamide Fumarate for HIV Pre-exposure Prophylaxis. Pharm. Res. 33: 1649-1656.
8. J. U. N. P. o. H. A. (UNAIDS), 2016.
9. L. Baert, G. van't Klooster, W. Dries, M. Francois, A. Wouters, E. Basstanie, K. Iterbeke, F. Stappers, P. Stevens, L. Schueller, P. Van Remoortere, G. Kraus, P. Wigerinck and J. Rosier. 2009. Development of a long-acting injectable formulation with nanoparticles of rilpivirine (TMC278) for HIV treatment. Eur. J. Pharm. Biopharm. 72: 502-508.

10. R. J. Landovitz, R. Kofron and M. McCauley. 2016. The Promise and Pitfalls of Long Acting Injectable Agents for HIV Prevention. Current opinion in HIV and AIDS. 11: 122-128.

11. J. G. García-Lerma and W. Heneine. 2012. Animal models of antiretroviral prophylaxis for HIV prevention. Current opinion in HIV and AIDS. 7: 505-513.

12. M. S. Widmer, P. K. Gupta, L. Lu, R. K. Meszlenyi, G. R. D. Evans, K. Brandt, T. Savel, A. Gurlek, C. W. Patrick and A. G. Mikos. 1998. Manufacture of porous biodegradable polymer conduits by an extrusion process for guided tissue regeneration. Biomaterials. 19: 1945-1955.

13. C.-K. Wang, W.-Y. Wang, R. F. Meyer, Y. Liang, K. I. Winey and S. J. Siegel. 2010. A rapid method for creating drug implants: translating laboratory-based methods into a scalable manufacturing process. Journal of biomedical materials research. Part B, Applied biomaterials. 93: 562-572.

14. C. Rabin, Y. Liang, R. S. Ehrlichman, A. Budhian, K. L. Metzger, C. Majewski-Tiedeken, K. I. Winey and S. J. Siegel. 2008. In vitro and in vivo demonstration of risperidone implants in mice. Schizophr. Res. 98: 66-78.

15. S. J. Siegel, J. B. Kahn, K. Metzger, K. I. Winey, K. Werner and N. Dan. 2006. Effect of drug type on the degradation rate of PLGA matrices. Eur. J. Pharm. Biopharm. 64: 287-293.

16. C. Ozioko, Manufacture of Tablets by Direct Compression Method, https://www.pharmapproach.com/manufacture-of-tablets-by-direct-compression-method-2/, 2018.

17. M. Jivraj, L. G. Martini and C. M. Thomson. 2000. An overview of the different excipients useful for the direct compression of tablets. Pharmaceutical Science & Technology Today. 3: 58-63.

What is claimed is:

1. A method of making a polymeric implant comprising forming a homogeneous drug-loaded polymer, wherein forming the homogenous drug-loaded polymer comprises:
   utilizing a phase inversion technique to produce an insoluble solid composition, the phase inversion technique comprising introducing a solution to an aqueous medium, the solution comprising (a) a biodegradable polymer, wherein the biodegradable polymer is poly (lactic-co-glycolic acid) (PLGA), (b) a water miscible biocompatible organic solvent, wherein the water miscible biocompatible organic solvent comprises N-methyl-2-pyrrolidone (NMP), (c) at least one pharmaceutically active agent, and optionally (d) a release rate-limiting additive, wherein the ratio of biodegradable polymer to water miscible biocompatible organic solvent in the solution is from 1:2 to 1:6, wherein the solvent diffuses into the aqueous medium during phase inversion causing the polymer and active agent to precipitate, providing the insoluble solid composition comprising the pharmaceutically active agent and the polymer;
   completely removing residual water miscible biocompatible organic solvent from the insoluble solid composition, thereby providing a dry insoluble composition;
   micronizing the dry insoluble solid composition; and
   utilizing direct compression of the micronized dry insoluble solid composition to form a solid tablet forming the polymeric implant.

2. The method claim 1, wherein the at least one pharmaceutically active agent is selected from the group consisting of an analgesic agent; an anti-anxiety agent; an anti-arthritic agent; an anti-asthmatic agent; an anticancer agent; an anticholinergic agent; an anticholinesterase; an anticonvulsant; an antidepressant; an antidiabetic agent; an antidiarrheal agent; an anti-emetic agent; an antihistamine; an antihyperlipidemic agent; an anti-infective agent; an anti-inflammatory agent; an antimigraine agent; an anti-obesity agent; an antipruritic agent; an antipsychotic agent; an antiretroviral agent, an antispasmodic agent; an agent for treating a neurodegenerative disease; a cardiovascular medicament; contraceptive agent, a diuretic agent; a gastrointestinal medication; a hormone or anti-hormone; a hypnotic agent; an immunosuppressive agent; a leukotriene inhibitor; a narcotic agonist or antagonist; a neurotransmitter; a nucleic acid; a nutrient; a peptide drug; a nutrient; a sympathomimetic agent; a thrombolytic agent; a vasodilator; or a combination thereof.

3. The method of claim 1, wherein the at least one pharmaceutically active agent is at least one antiretroviral agent.

4. The method of claim 2, wherein the at least one pharmaceutically active agent comprises a contraceptive agent.

5. The method of claim 1, wherein the water miscible biocompatible organic solvent is NMP or wherein the water miscible biocompatible organic solvent is a co-solvent system consisting of NMP and a co-solvent, wherein the ratio of NMP to cosolvent is 9:1.

6. A polymeric implant formed according to the method of claim 1.

7. A controlled release drug delivery system comprising an implantable or administered device that provides controlled release of at least one pharmaceutically active agent throughout an extended drug delivery time period, the implantable device comprising a drug-loaded polymer formed by a process comprising:
   utilizing a phase inversion technique to produce an insoluble solid composition, the phase inversion technique comprising introducing a solution to an aqueous medium, the solution comprising (a) a biodegradable polymer, wherein the biodegradable polymer is poly (lactic-co-glycolic acid (PLGA), (b) a water miscible biocompatible organic solvent, wherein the water miscible biocompatible organic solvent comprises N-methyl-2-pyrrolidone (NMP), (c) at least one pharmaceutically active agent, and optionally (d) a release rate-limiting agent, wherein the ratio of biodegradable polymer to water miscible biocompatible organic solvent in the solution is from 1:2 to 1:6, wherein the solvent diffuses into the aqueous medium during phase inversion to cause the polymer and active agent to precipitate to provide the insoluble solid composition comprising the pharmaceutically active agent and the polymer;
   completely removing residual water miscible biocompatible organic solvent from the insoluble solid composition, thereby providing a dry insoluble composition;
   micronizing the dry insoluble solid composition; and
   utilizing direct compression of the micronized dry insoluble solid composition to form a solid tablet forming the implantable or administered device,
   wherein following implantation or administration of the device into a subject, the device results in a serum level of the pharmaceutically active agent sufficient to achieve therapeutic efficacy during the extended drug delivery time period.

8. The drug delivery system of claim 7, wherein the insoluble solid composition comprising the pharmaceutically active agent and the polymer is formed in situ.

9. The drug delivery system of claim 7, wherein multiple pharmaceutical agents are combined in a single tablet or a sandwiched tablet.

10. The drug delivery system of claim 7, wherein the at least one pharmaceutically active agent is selected from the group consisting of an analgesic agent; an anti-anxiety agent; an anti-arthritic agent; an anti-asthmatic agent; an anticancer agent; an anticholinergic agent; an anticholinesterase; an anticonvulsant; an antidepressant; an antidiabetic agent; an antidiarrheal agent; an anti-emetic agent; an antihistamine; an antihyperlipidemic agent; an anti-infective agent; an anti-inflammatory agent; an antimigraine agent; an anti-obesity agent; an antipruritic agent; an antipsychotic agent; an antiretroviral agent, an antispasmodic agent; an agent for treating a neurodegenerative disease; a cardiovascular medicament; a contraceptive agent, a diuretic agent; a gastrointestinal medication; a hormone or anti-hormone; a hypnotic agent; an immunosuppressive agent; a leukotriene inhibitor; a narcotic agonist or antagonist; a neurotransmitter; a nucleic acid; a nutrient; a peptide drug; a nutrient; a sympathomimetic agent; a thrombolytic agent; a vasodilator; or a combination thereof.

11. The drug delivery system of claim 7, wherein the at least one pharmaceutically active agent is at least one antiretroviral agent.

12. The drug delivery system of claim 10, wherein the at least one pharmaceutically active agent comprises a contraceptive agent.

13. The drug delivery system of claim 7, wherein the at least one pharmaceutically active agent is released at a rate that is substantially constant throughout the effective drug delivery time period.

14. The drug delivery system of claim 7, wherein the effective drug delivery time period is in the range of about six months to about to about 1 year.

\* \* \* \* \*